(12) United States Patent
Noble et al.

(10) Patent No.: US 7,043,063 B1
(45) Date of Patent: May 9, 2006

(54) NON-RIGID MOTION IMAGE ANALYSIS

(75) Inventors: Julia Alison Noble, Oxford (GB); Gary Jacob, London (GB)

(73) Assignee: Mirada Solutions Limited, Oxfordshire (GB)

( * ) Notice: Subject to any disclaimer, the term of this patent is extended or adjusted under 35 U.S.C. 154(b) by 617 days.

(21) Appl. No.: 10/069,291

(22) PCT Filed: Jul. 19, 2000

(86) PCT No.: PCT/GB00/02767

§ 371 (c)(1),
(2), (4) Date: Mar. 12, 2002

(87) PCT Pub. No.: WO01/16886

PCT Pub. Date: Mar. 8, 2001

(30) Foreign Application Priority Data

Aug. 27, 1999 (GB) .................................... 9920401

(51) Int. Cl.
*G06K 9/00* (2006.01)
(52) U.S. Cl. ...................... 382/128; 382/107; 382/173; 382/241
(58) Field of Classification Search ................ 382/128, 382/107, 131, 132, 173, 180, 190, 192, 199
See application file for complete search history.

(56) References Cited

U.S. PATENT DOCUMENTS

| | | | |
|---|---|---|---|
| 4,760,548 A * | 7/1988 | Baker et al. ................ | 708/270 |
| 5,054,045 A | 10/1991 | Whiting et al. | |
| 5,090,042 A | 2/1992 | Bejjani et al. | |
| 5,214,382 A | 5/1993 | Harms et al. ................ | 324/309 |
| 5,293,574 A | 3/1994 | Roehm et al. | |
| 5,435,310 A * | 7/1995 | Sheehan et al. ............. | 600/416 |
| 5,546,476 A | 8/1996 | Mitaka et al. .............. | 382/201 |
| 5,669,382 A | 9/1997 | Curwen et al. | |
| 5,825,936 A * | 10/1998 | Clarke et al. ................ | 382/261 |
| 6,157,677 A | 12/2000 | Martens et al. ......... | 375/240.16 |
| 2004/0047498 A1 | 3/2004 | Mulet-Parada et al. ..... | 382/128 |
| 2004/0094167 A1 | 5/2004 | Brady et al. ................ | 128/916 |

FOREIGN PATENT DOCUMENTS

| | | |
|---|---|---|
| EP | 652536 A2 | 5/1995 |
| GB | 2 268 351 | 1/1994 |
| GB | 2 269 508 | 2/1995 |
| JP | 10-165401 A | 6/1998 |
| WO | 95/26539 | 10/1995 |
| WO | 00/57361 | 9/2000 |

OTHER PUBLICATIONS

Chalana et al; "A Mutliple Active Contour Model for Cardiac Boundary Detection on Echocardiographic Sequences"; IEEE Transactions on Medical Imaging, vol. 15, No. 3, Jun. 1, 1996, pp. 290-298.*

(Continued)

*Primary Examiner*—Brian Werner
*Assistant Examiner*—Christopher Lavin
(74) *Attorney, Agent, or Firm*—Nixon & Vanderhye, PC

(57) ABSTRACT

A method of analysing a sequence of images of a deformable object in non-rigid motion involves modeling the boundary using a non-rigid contour. A representation of movement of the contour through the sequence of images is calculated using a tracking space shape. The calculated movement representation is decomposed using an interpretational space shape that is different than the tracking space shape.

48 Claims, 19 Drawing Sheets

OTHER PUBLICATIONS

Jacob et al; "Robust Contour Tracking in Echocardiographic Sequences" Sixth Internation Conference on Computer Vision, Processing of IEEE 6th Internation Conference on Computer Vision, Bombay Jan. 4-7, 1998; pp. 408-413.*

Setarehdan et al; "Automatic Left Ventriclular Feature Extraction and Visualisation from Echocardiographic Images"; Computers in Cardiology, 1996, pp. 9-12.*

Foley, Thomas; "Interpolation with Interval and Point Tension Controls Using Cubic Weighted v-Splines"; ACM Transactions on Mathematical Software, vol. 13, No. 1 Mar. 1987, pp. 68-96.*

McEachen JC II et al; "Shape-Based Tracking of Left Ventricular Wall Motion"; IEEE Transactions on Medical Imaging, Jun. 1997, vol. 16, No. 3, pp. 270-283, XP002155446.

Setarehdan SK et al; "Automatic Left Ventricular Feature Extraction and Visualisation From Echocardiographic Images"; Computers in Cardiology, 1996, pp. 9-12, XP000687747.

Jacob G et al; "Robust Contour Tracking in Echocardiographic Sequences" Sixth International Conference on Computer Vision (IEEE CAT. No. 98CH36271), Processing of IEEE 6$^{th}$ International Conference on Computer Vision, Bombay, Jan. 4-7, 1998; pp. 408-413, XP002155450.

Chalana V et al; "A Multiple Active Contour Model for Cardiac Boundary Detection on Echocardiographic Sequences"; IEEE Transactions on Medical Imaging, vol. 15, No. 3, Jun. 1, 1996, pp. 290-298, XP000587923.

Kass M et al; "Snakes: Active Contour Models"; London, Jun. 8-11, 1987, Washington, IEEE Comp. Soc. Press, vol. CONF. 1, Jun. 8, 1987, pp. 259-268, XP000971219.

Kita et al., "Correspondence Between Different View Breast X-Rays Using a Simulation of Breast Deformation"; Proceedings 1998 IEE Computer Society Conference on Computer Vision and Pattern Recognition, Santa Barbara, CA, Jun. 23-25, 1998, pp. 700-707, XP002169274.

Strickland et al., Computing Correspondence in a Sequence of Non-Rigid Shapes, Pattern Recognition, Pergamon Press Inc., Elmsford, NY, vol. 25, No. 9, Sep. 1, 1992, pp. 901-912.

Cham et al., "A Statistical Framework for Long-Range Feature Matching in Uncalibrated Image Mosaicing", Computer Vision and Pattern Recognotion, Proceedings 1998 IEEE Computer Society Conference on Jun. 23-25, 1998, pp. 442-447.

Jianzin Hou et al; "Orientation Selective Operators for Ridge, Valley Edge, and Line Detection in Imagery"; Proceedings of the International Conference on Acoustics, Speech and Signal Processing (ICASSP). I. Image and Multidimensional Signal Processing. Adelaide, Apr. 19-22, 1994, New York, IEEE, US, vol. 5, Conf. 19, pp. V-25-V-28, XP000533688.

Vega-Riveros et al; "Review of Motion Analysis Techniques"; IEE Proceedings I. Solid-State & Electron Devices, Institution of Electrical Engineers, Stevenage, GB, vol. 136, No. 6, Part 1, Dec. 1, 1989, pp. 397-404, XP000080261.

Cucchiara et al: "Detection of Luminosity Profiles of Elongated Shapes"; Proceedings of the International Conference on Image Processing (ICIP) Lausanne, Sep. 16-19, 1996, New York, IEEE, US, vol. 1, pp. 6350638, XP010202474.

"Intensity-invariant 2D+T Acoustic Boundary Detection" is from the Workshop on Biomedical Image Analysis, Jun. 26-27, 1998, Santa Barbara, California.

Intensity-invariant 2D+T Acoustic Boundary Detection is from the Proceedings of Medical Image Understanding and Analysis 98, University of Leeds, Jul. 6-7, 1998.

"2D+T Acoustic Boundary Detection in Echocardiography" is from Medical Image Computing and Computer-Assisted Intervention—MICCAI'98 First International Conference Cambridge, MA, USA, Oct. 1998 Proceedings, printed in Lecture Notes in Computer Science, edited by William M Wells, Alan Colchester and Scott Delp.

Kita et al., "Correspondence Between Different View Breast X-Rays Using a Simulation of Breast Deformation"; Proceedings 1998 IEEE Computer Society Conference on Computer Vision and Pattern Recognition, Santa Barbara, CA, Jun. 23-25, 1998, pp. 700-707, XP002169274.

INSPEC Abstract Accession No. 6398151, Muller et al. Feb. 22, 1999.

Strickland et al., Computing Correspondence in a Sequence of Non-Rigid Shapes, Pattern Recognition, Pergamon Press Inc., Elmsford, NY, vol. 25, No. 9, Sep. 1, 1992, pp. 901-912.

Cham et al., "A Statistical Framework for Long-Range Feature Matching in Uncalibrated Image Mosaicing", Computer Vision and Pattern Recognotion, Proceedings 1998 IEEE Computer Society Conference on Jun. 23-25, 1998, pp. 442-447.

Jianzin Hou et al; "Orientation Selective Operators For Ridge, Valley Edge, and Line Detection in Imagery"; Proceedings of the International Conference on Acoustics, Speech and Signal Processing (ICASSP). I. Image and Multidimensional Signal Processing. Adelaide, Apr. 19-22, 1994, New York, IEEE, US, vol. 5, Conf. 19, Apr. 19, 1994, pp. V-25-V-28, XP000533688.

Vega-Riveros et al; "Review Of Motion Analysis Techniques"; IEEE Proceedings I. Solid-State & Electron Devices, Institution of Electrical Engineers, Stevenage, GB, vol. 136, No. 6, Part 1, Dec. 1, 1989, pp. 397-404, XP000080261.

* cited by examiner

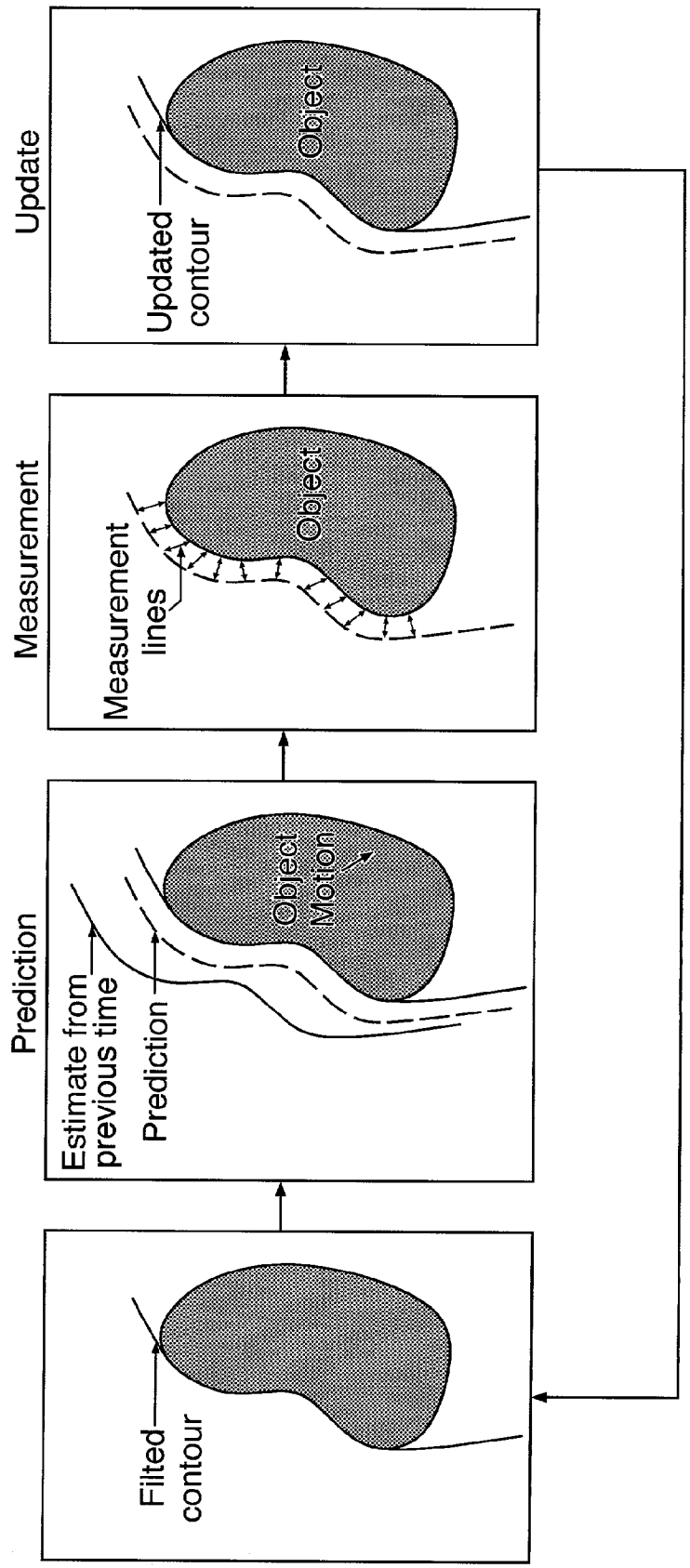

Fig. 10(B).
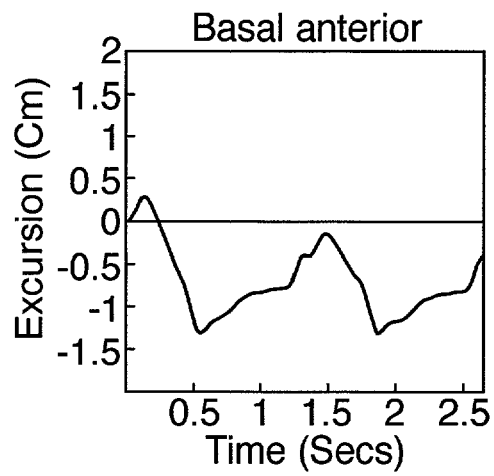
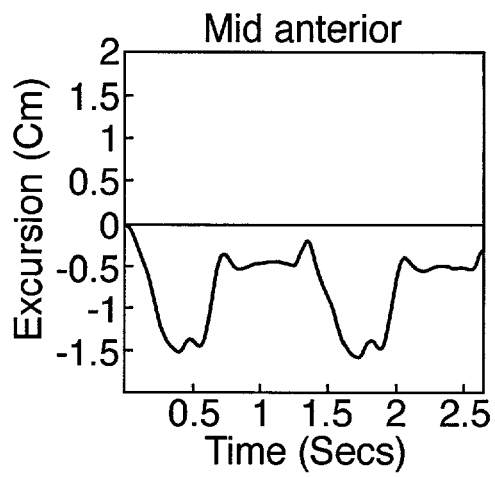
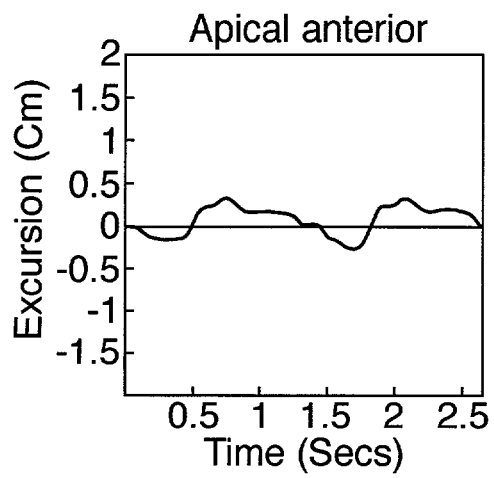
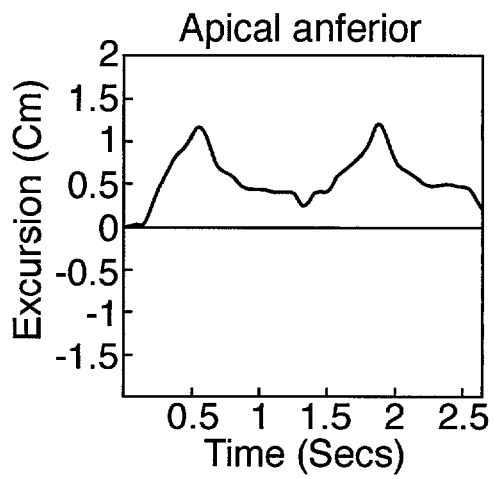
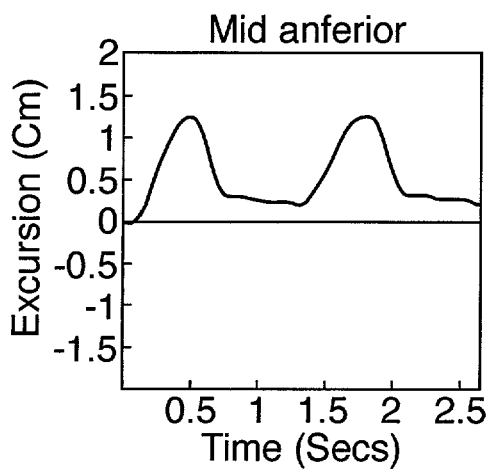
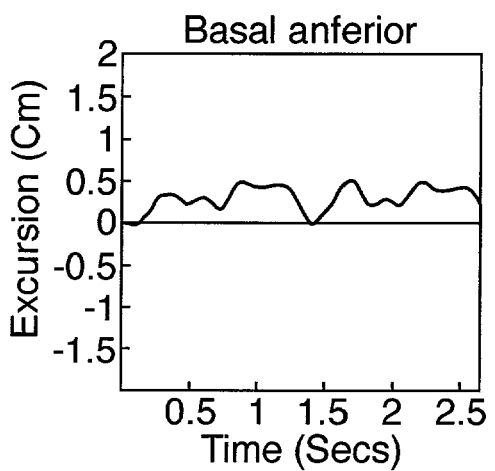

Maximal endocardial wall excursion (cm)

Normalised maximal endocardial wall excursion

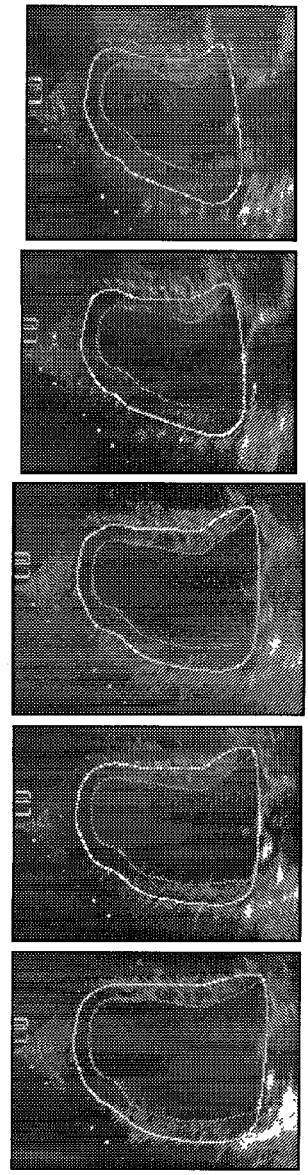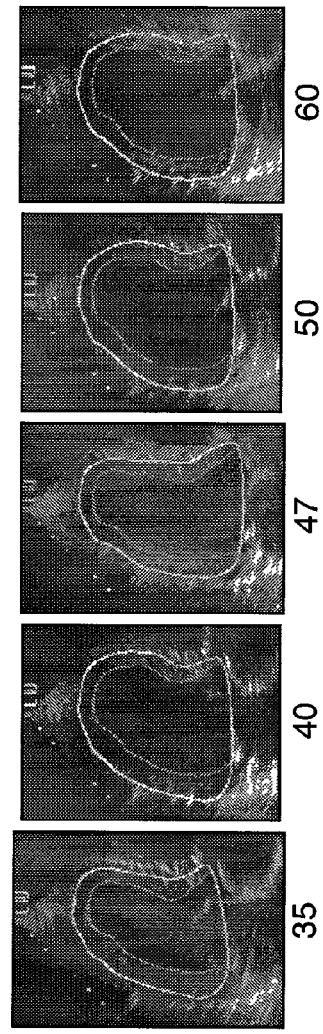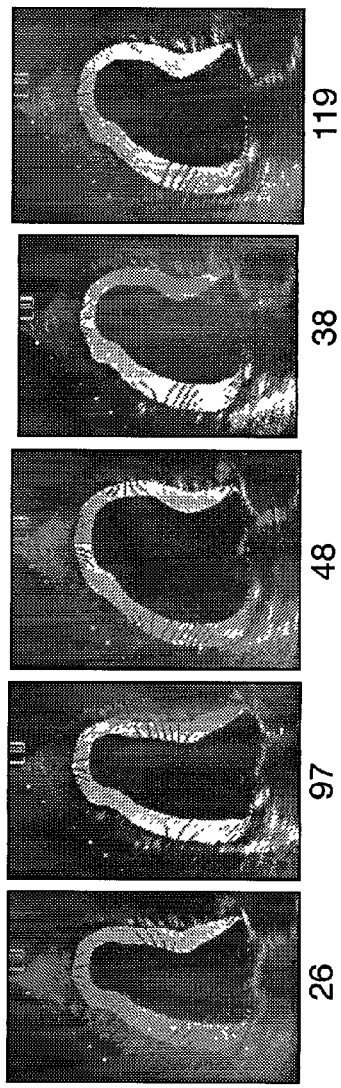
Fig. 18(A).
Fig. 18(B).

Fig.19.
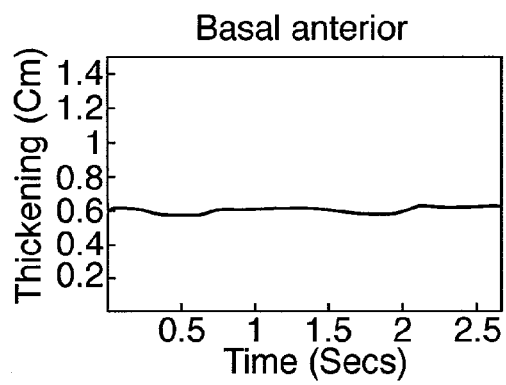
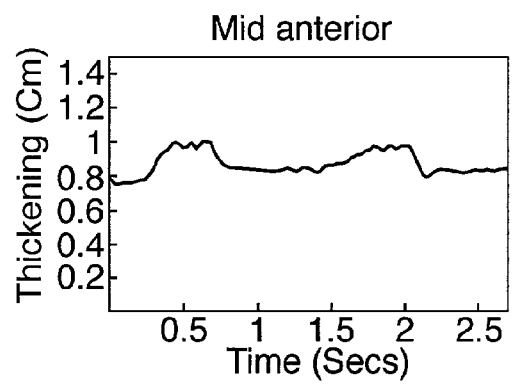
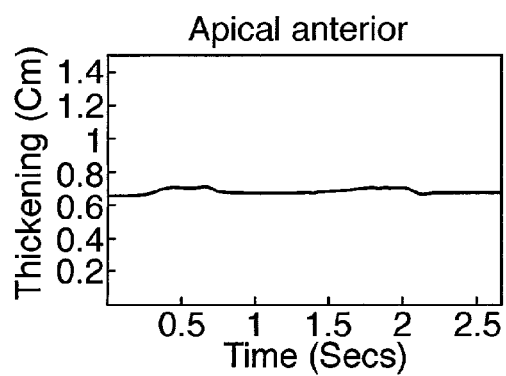
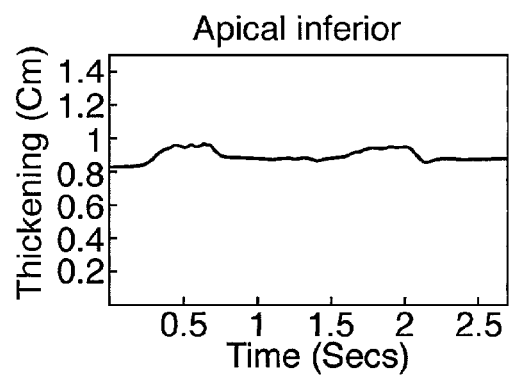
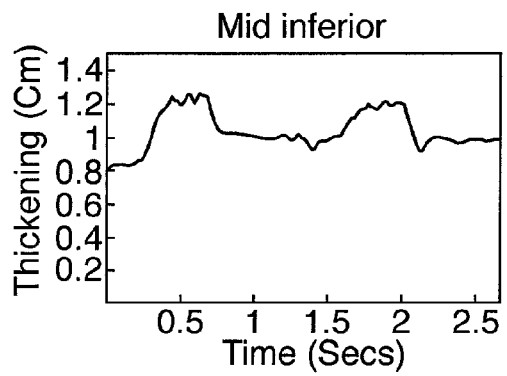
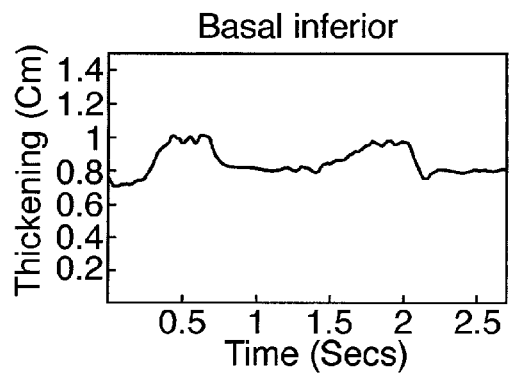

Normalised maximal endocardial wall excursion 0.71  0.34
0.77  0.92
0.31  1.00

Percentage myocardial thickening 0.16  0.09
0.55  0.33
0.43  0.09

NON-RIGID MOTION IMAGE ANALYSIS

This application is the US national phase of international application of PCT/GB00/02767 filed 19 Jul. 2000, which designated the US.

BACKGROUND AND SUMMARY

The present invention relates to a method of analysing images of a deformable object undergoing non-rigid motion. In particular it relates to a method of analysing the image so that desired image features can be detected and tracked through the sequence, and so that the motion of the features can be automatically quantified and analysed.

Basic techniques for analysing images of objects in motion are relatively straightforward for rigid motion, i.e. where the object does not itself deform. However, the analysis of non-rigid motion, where the object deforms in time, is more difficult. Such non-rigid motion occurs in many situations, but a typical one is in the medical or vetinary imaging field where organs of the human or animal body are imaged in real-time. As well as the problem created by the non-rigid motion of the organ being analysed, these imaging applications in particular have the additional problem that the images are very noisy. It is often difficult even for trained operators to find desired image features in the image, and thus reliable automatic detection of the features presents considerable difficulty.

In the field of cardiac imaging, various techniques are used such as multi-gated acquisition scanning (MUGA), fast computed tomography (CT), positron emission tomograph (PET), magnetic resonance imaging (MRI) and echocardiography (i.e. ultrasound imaging). Of these echocardiography is the most widely used because the imaging equipment is relatively cheap to obtain and maintain and the equipment is relatively portable.

In assessing cardiac function the performance of the left or right ventricle of the heart is particularly significant and there has been an increasing interest in obtaining ventricular measurements, such as the chamber dimensions, area, volume and ejection fraction. To provide a more accurate picture of the ventricular function, and in particular to enable assessment of abnormalities which occur in only parts of the ventricular wall, two particular aspects of the motion of the ventricle have proved significant. These are endocardial wall motion, also referred to as wall excursion, and myocardial wall thickening. It has been determined that when the heart muscle becomes ischemic (i.e. deficient in blood), its motion is altered almost immediately. Because abnormalities can be confined to particular parts of the ventricular wall, a systematic method for the assessment of wall motion involves the segmentation of the surface into a number of different segments. The wall can be segmented in various ways, but a useful method is the sixteen-segment anatomical model of the heart proposed by the American Society of Echocardiography and illustrated in FIG. 8 of the accompanying drawings. This is useful in assessing the images derived from two-dimensional echocardiography.

FIG. 8(*d*) shows an example of a view which is used for analysis in the techniques described below. In assessing cardiac function for instance of the left ventricle clinicians examine the motion and thickening of each segment and try to assess visually the motion of each segment through the heart cycle. One scoring scheme requires the clinician to score each segment as follows:

| Score | Grading | Characterized by |
| --- | --- | --- |
| 1 | Normal | A uniform increase in wall excursion and thickening |
| 2 | Hypokinetic | A reduced (<5 mm) inward systolic wall motion |
| 3 | Akinetic | An absence of inward motion and thickening |
| 4 | Dyskinetic | Systolic thinning and outward systolic wall motion |

However, this scoring scheme is highly subjective. Thus clinical reporting of echocardiography examination is highly operator-dependent and basically qualitative. Also each segment must be classified as normal or abnormal, so it is difficult for a clinician to indicate within the scoring system subtleties such as only part of a segment being abnormal.

While there is therefore a clear need for an automatic method of detecting and quantifying wall motion and wall thickening, the images are extremely difficult to assess automatically. In the accompanying drawings FIGS. 1(*a*) to (*d*) show a typical set of echocardiographic images. FIG. 1(*a*) shows an image digitized from a video recording; FIG. 1(*b*) shows an image obtained from one of the latest ultrasound machines; FIG. 1(*c*) shows a stress echocardiography image of a patient at rest and FIG. 1(*d*) shows the same patient as in FIG. 1(*c*) at a peak dose of dobutamine (a drug which mimics the effects of exercise). It will be appreciated that identifying the desired regions of the ventricle is difficult for a human, and that automatic analysis is even more difficult.

Automatic boundary detection of regions in an ultrasound image is available on certain machines manufactured by Hewlett-Packard by a technique known as acoustic quantification (AQ). This technique discriminates boundaries prior to image formation by using discontinuities in the signal returning from the tissue. Pixels with an intensity gradient above a user-defined threshold are marked as boundary points. Pixels labelled as boundary points are then joined together to form connected boundaries. However, FIGS. 2(*a*)–(*d*) show that this technique is not always useful. FIGS. 2(*a*) and (*c*) show the basic echocardiographic image, and FIGS. 2(*b*) and 2(*d*) show the corresponding respective AQ images at different thresholds. It can be seen that the illustrated boundaries do not help assessment of the image at all because they do not accurately follow the real boundaries.

A better method for detecting the inner boundary of the left ventricle (the endocardium) is proposed in the paper "Evaluating A Robust Contour Tracker On Echocardiographic Sequences" by Jacob, Noble, Mulet-Parada and Blake, published in Medical Image Analysis (1997/8 volume 3, number 1, pp 63–75) which is hereby incorporated by reference. As proposed there the inner boundary, endocardium, is modelled by a non-rigid contour (a B-spline) and the variation in the shape of this contour through the echocardiographic sequence (i.e. as the heart contracts and expands) is represented by using a shape-space. This means that the position of the endocardial wall in each image is regarded as being composed of a time varying departure from a defined position e.g. the initial position, the departure being characterised as a time-varying weighted sum of certain basic types of motion of the contour. For instance, a very simple shape-space would characterise the motion of an object as consisting of a certain proportion of rotation and a certain proportion of translation compared to a defined position. Then the only thing which varies with time is the relative amount of the rotation and translation. In analysing echocardiograms a more complicated shape space has been found to be necessary. The paper referred to above uses a principal component analysis (PCA) of the motion of the endocardial wall to find a set of define motions which can efficiently be used as components to approximate the actual motion of the endocardial wall. Again, the only thing which varies through the sequence is the relative weight of the different define motions in each image.

In this technique for detecting and tracking the endocardial wall, the clinician is required first to examine the frames of the image sequence and manually to locate and trace in a few of the frames the endocardial wall. For instance, in a sequence of 60–80 frames the clinician could manually "draw around" the endocardial boundary every fifth frame. A B-spline curve is then fitted to the manually traced contours to provide an approximation of them and a principal component analysis is performed to find the define components of the motion of the contour through the image sequence. Then the whole sequence is reprocessed so that starting from a predefined initial position the position of the endocardial wall in each frame is predicted based on the position in the preceding two frames and the PCA results. The prediction is corrected in each frame by searching for image features (such as intensity edges) representing the actual position of the endocardial wall. When this process is complete, the B-spline curve for each frame can be displayed overlying the image on that frame so that when the sequence is displayed the contour appears to track the endocardial wall through the sequence.

Illustrating this in more detail, it will be recalled that the shape of a B-spline curve is determined by the position of its control points. Thus the movement of a spline curve fitted to the endocardial wall through the image sequence can be expressed entirely as a change from frame to frame of the position of the control points of the spline curve. The x and y coordinates of the control points are conventionally written in a matrix known as a spline-vector Q and as discussed above, the position of the control points in any frame of the sequence can be expressed as an offset from a defined position $Q_0$. The offset, which is time-varying, can conveniently be separated into a time-varying part known as the shape-space vector X and a part representing the type of allowed motions (the main components of the motion), known as the shape matrix W (normally assumed to be constant).

Thus, in matrix notation:—

$$Q = Q_0 + WX$$

In order to find the spline curve which fits to the endocardial boundary in every frame of the sequence (which amounts to finding the position of the control points of the curve in every frame of the sequence) the first step is that the clinician manually draws around the boundary in several frames, for instance every fifth frame. Then a B-spline curve is fitted to the drawn boundary using a user-defined number of control points. FIG. 3(a) shows a schematic representation of a quadratic approximating B-spline with 24 control points used to model the endocardial boundary. FIG. 3(b) illustrates the curve superimposed on a frame of an ultrasound image. A principal component analysis is then performed on the positions of the control points in each of the frames segmented by the clinician to calculate $Q_0$ and W. The aim then is to find the position of the endocardial boundary in all of the frames of the sequence automatically, i.e. without requiring the clinician manually to draw around them. FIG. 4 illustrates the process schematically. The process involves predicting the position of the boundary each frame based on the boundary in the preceding frames. In other words the value of X (the shape-vector) which is the only time varying part is predicted based on the value in the preceding two frames. Then a search is performed around the predicted position to find image features representative of the actual position of the endocardial boundary. In this technique the searches are performed along a plurality of normals spaced along the predicted curve and the image features are identified through known image processing operations, such as looking at the intensity variation along the search line. When the image features corresponding to the boundary have been found the predicted position can be updated and the actual position of the contour (expressed through the position of the control points of the B-spline) is established.

It will be understood that having represented the endocardial boundary as a B-spline, the only time varying part through the sequence is the position of the control points and, in the shape-space representation, the shape-vector X. It will be recalled that the elements of X are the weights of the different types of motion (i.e. the different principal components of the motion) found in the principal component analysis.

FIG. 5 illustrates an example of a principal component analysis performed on four cardiac cycles of an ultrasound image sequence using a B-spline with 14 control points. The six most dominant modes are shown, each is shown as an initial template (thick solid line) and the change in shape represented by that component of the motion is indicated by the thin solid lines. The diagram in the top left of FIG. 5 is the dominant mode and that in the bottom mode is the least dominant. The deformation represented by each mode is shown in an alternative way in FIG. 6 where a flow vector is centred at the start of each span of the spline curve and shows the movement of that part of the curve. Thus the motion of the contour (spline curve) through the image sequence which was analysed can be expressed as a sum of these motions. The position of the curve in any frame represents a certain weighted sum of these motions. The weights are the values of the components of X and thus the motion can be expressed entirely by looking at the time variation of the components of X. The variation of X with time is illustrated for an echocardiogram sequence in FIG. 7. FIG. 7(a) shows the PCA based components for this sequence and FIG. 7(b) shows the values of the weights versus time of each of those components. It is, however, difficult to interpret clinically the significance of these components and weights. For example, the first deformation mode in FIG. 7(a) (top left) appears to be a scaling of the inferior part of the left ventricular boundary. The corresponding plot of the weight of that component illustrates that this motion is basically periodic. But because this component of the motion affects more than just a single part of the boundary (all parts of the boundary move) it does not give a good idea of how any particular region of the wall is moving. Also, some of the information about the motion of that part of the boundary is "encoded" in the other components.

Thus although the principal component analysis, which gives the component magnitudes of the shape-space vector X is very useful in tracking, it does not provide a good basis for automatic interpretation of the results.

It was mentioned above that wall-thickening, known as myocardial thickening is also a clinically significant factor in assessing the condition of the heart. As the heart is beating the ventricle expands and contracts, predominately by periodic thickening of the ventricular wall. If the wall fails to thicken then the ventricular volume will not change by so great an amount and the pumping of blood will be reduced. Thus it would be advantageous to be able to quantitatively analyse the degree of thickening of the ventricular wall. It may be thought that this could straightforwardly be done by detecting the outer (epicardial) boundary of the ventricular wall, in just the same way as the inner (endocardial) boundary is detected above. However, the endocardial boundary (the inner boundary) is a boundary between muscle and blood which have quite different acoustic impedances. In general this means that the endocardial boundary shows up well on an echocardiogram. The epicardial boundary on the other hand is a tissue—tissue interface and so it is very difficult to trace on the image.

Thus even having tracked the endocardial boundary, it is difficult to detect and quantitatively analyse the movement of the epicardial boundary.

The present invention provides techniques which are useful in solving these two problems. Although illustrated in use in analysing echocardiograms of the left ventricle the techniques are not limited to this. They are applicable to analysis of non-rigid motion in two or three dimensions of other deformable objections. Thus they have other medical and vetinary applications as well as being applicable to imaging deformable objects in general and are also applicable to image modalities other than ultrasound.

The first aspect of the present invention provides a method of analysing a sequence of images of an internal body organ in non-rigid motion, comprising the steps of: detecting the boundary of the organ in each image of the sequence; and automatically calculating the amount of movement through the sequence of each of a plurality of clinically significant segments of the detected boundary.

The amount of movement of each of the clinically significant segments, which can be the segments illustrated in FIG. 8, preferably those in FIG. 8(d), can be displayed graphically, for instance as a graph. Further, an average of the amount of movement of that segment can be calculated as a single number representative of the amount of movement of that segment. It is also possible to calculate the variation in the amount of movement in a segment, the greater the variation, the more likely it is that only a part of that segment is normal. It is also possible to calculate and output the maximal excursion of the detected boundary during the motion, for each segment.

Preferably the boundary is detected and tracked by the technique of principal component analysis and fitting of a spline curve as described above.

The amount of movement of the segments can conveniently be found by calculating and outputting for each segment a measure of the amount of movement of the control points controlling the curve within that segment. This measure may be a simple average, or can be weighted in favour of the control points in the middle of each segment.

The variation in the amount of movement within the segment is conveniently found by comparing the amount of movement of the different spline curve control points for that segment.

These measures can easily be obtained from the position of the control points in each frame of the sequence by defining a new shape-space, different from that used in the tracking process, and calculating from the control points the shape-vector corresponding to the different shape-space. The new shape-space can be selected to ensure that each component of the shape-vector represents the amount of movement of control points in a single clinically significant segment only. Then displaying graphically the time varying components of the new shape-vector gives a good indication of the motion of that segment. This aspect of the invention is particularly applicable to analysing ultrasound images of a heart, e.g. of the left or right ventricle.

The invention also contemplates the interpretation of a moving spline curve tracked in one shape-space by using a different shape-space. Thus another aspect of the invention provides A method of analysing a sequence of images of a deformable object in non-rigid motion comprising the steps of detecting a boundary of the object in each of a plurality of frames of the sequence, fitting a spline curve to the boundary in constructing a shape space representation of the movement of spline curve using a first shape space so that the spline curve tracks the boundary, and decomposing the tracking spline curve using a second different, shape space. The different shape-space can be chosen to select a particular attribute of the motion. In other words, a motion tracked using one shape-space need not be interpreted in the same shape-space: a different one—an interpretational shape-space can be used.

Another aspect of the invention involves the modelling of the configuration of the wall of an object having two boundaries as seen in a sequence of images by developing a model of the distance between the two boundaries. Thus rather than modelling each boundary separately, a model is constructed for the distance between them. Thus this aspect of the invention provides a method of analysing a sequence of images of a deformable object in non-rigid motion comprising detecting first and second boundaries of the object in a plurality of frames of the sequence and constructing a shape space representation of the variation through the sequence of the distance between the two boundaries.

The model can be a shape-space of the change in distance between the boundaries, and can be based on a principal component analysis of the way that distance changes. The model can be improved by searching the images to find image features representative of the outer boundary. The model avoids incorrect results such as the outer boundary crossing inside the inner boundary.

Another aspect of the invention provides a method of analysing a sequence of images of a deformable object in non-rigid motion to detect inner and outer boundaries of a wall of the object, comprising the steps of: detecting the inner boundary; and searching outside the inner boundary for image features representing the outer boundary.

Thus because it is known that the inner boundary will be inside the outer boundary, this provides a useful start point for the search of the image features representing the outer boundary.

Preferably a spline curve is fitted to the detected image features representing the outer boundary, e.g. by: manually locating the inner and outer boundaries in only some images of the sequence, calculating a shape-space for the change through the sequence of the distance between the two boundaries, detecting the inner boundary and performing said search outside the inner boundary for image features representing the outer boundary in other images of the sequence; and fitting a spline curve to the detected image features in said other images of the sequence by using said shape-space.

Thus in this method a shape-space representing the distance between the two boundaries is obtained. The use of this shape-space helps to ensure that the calculated outer boundary always lies outside the inner boundary. The distance between the two boundaries in the manually treated frames can be subjected to a principal component analysis which is used as a basis for the shape space. This then provides a convenient model of the deformation of the object wall.

The search for the image features representing the outer boundary can be, for instance, by analysing changes in the image intensity, such as a maximum in the intensity, along search lines projected outwards from the inner boundary. In certain images the plot of the intensity can be extremely noisy and it can be rather difficult to detect a clear maximum. In this case a wavelet decomposition of the profile of image intensity can be performed to smooth the profile.

To obtain a better fit to the actual outer boundary, it is possible to apply extra conditions to the fitting. For instance, detected image features can be down weighted if they imply a curvature of the outer boundary which is too high. Similarly, features can be weighted down if they imply a difference between the inner and outer boundaries which lies outside the shape-space.

This technique is particularly useful for the analysis of ultrasound images, in particular of the heart, e.g. of the left or right ventricle. In that case the distance between the inner and outer boundaries represents the myocardial thickness and the change in that thickness through an image sequence is indicative of the condition of the heart.

Again, the ventricular wall can be segmented according to the FIG. 8 model and the degree of thickening for each separate segment can calculated and graphically displayed, as can the variation within each segment.

It will be appreciated that the methods of the invention are conveniently embodied in a computer program, and thus the invention provides a computer program and computer system for performing the methods above.

BRIEF DESCRIPTION OF THE DRAWINGS

The invention will be further described by way of a non-limitative example with reference to the accompanying drawings in which:—

FIG. 4 schematically illustrates a tracking process;

FIG. 10(b) illustrates the variation with time of the components in an interpretational shape-space;

FIG. 18(a) illustrates the results of the track endocardial and epicardial walls and FIG. 18(b) illustrates the myocardium shaded;

FIG. 19 illustrates the wall thickening for each segment through the image sequence;

DETAILED DESCRIPTION OF EXAMPLE EMBODIMENTS

Figure 1A:
FIGS. 1(a) to (d) show a typical set of echocardiographic images.
Figure 1B:
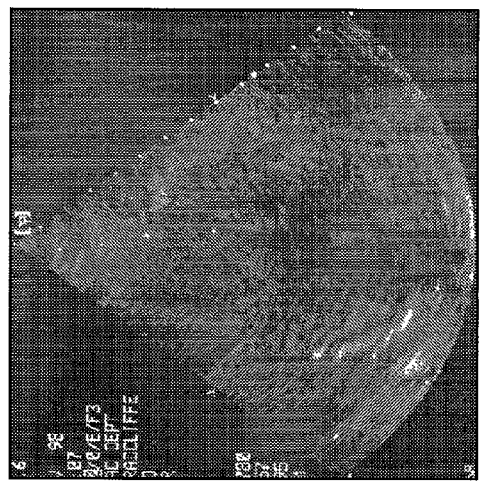
Figure 1C:
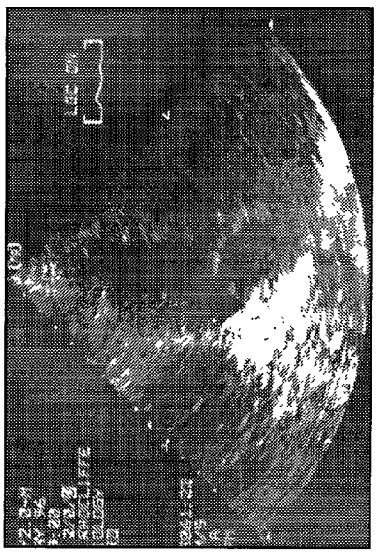
Figure 1D:
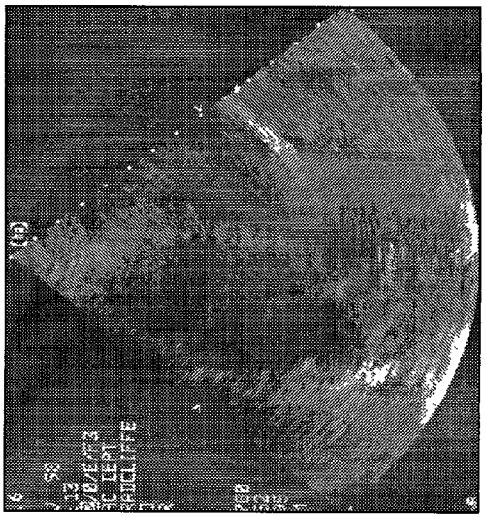
Figure 2A:
FIGS. 2(a) to (d) illustrate define echocardiographic images and respective AQ images.
Figure 2B:
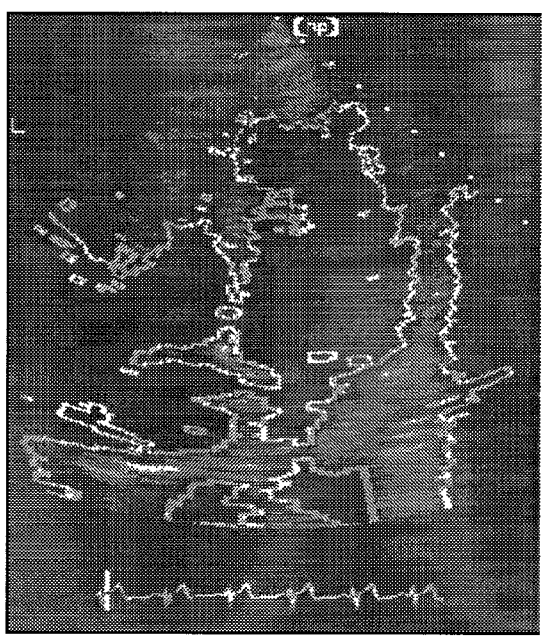
Figure 2C:
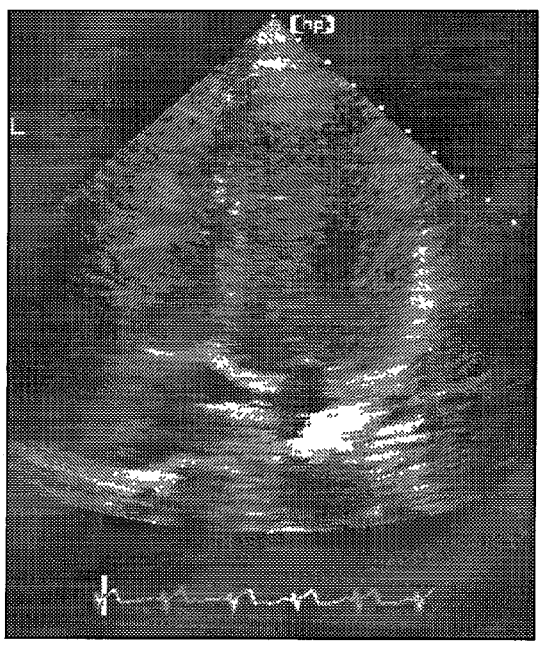
Figure 2D:
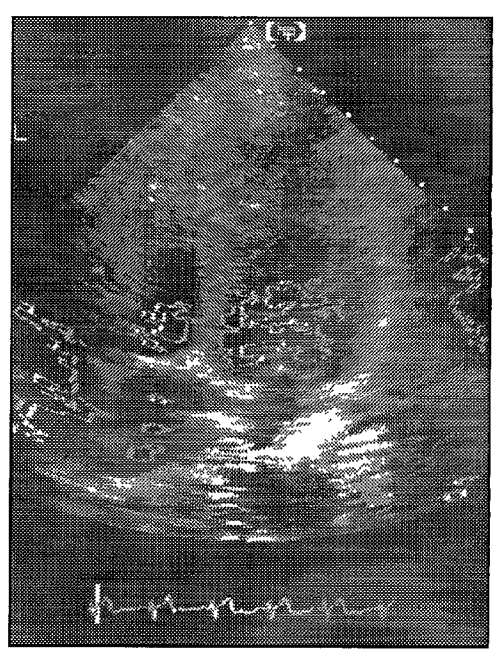
Figure 3A:
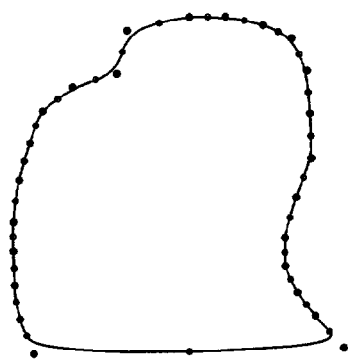
FIG. 3(a) shows a schematic representation of a quadratic approximating B-spline.
Figure 3B:
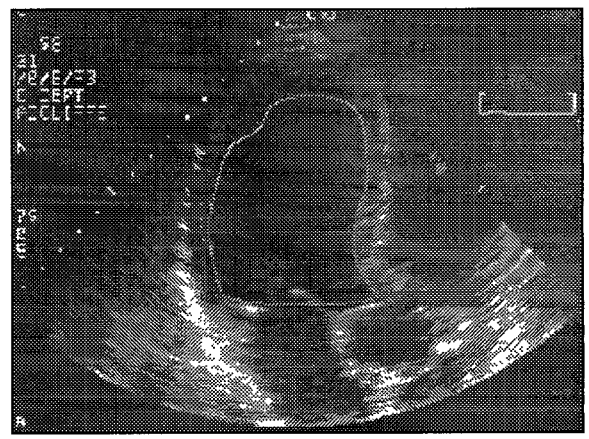
FIG. 3(b) illustrates the B-spline of FIG. 3(a) superimposed on an ultrasound image.
Figure 5:
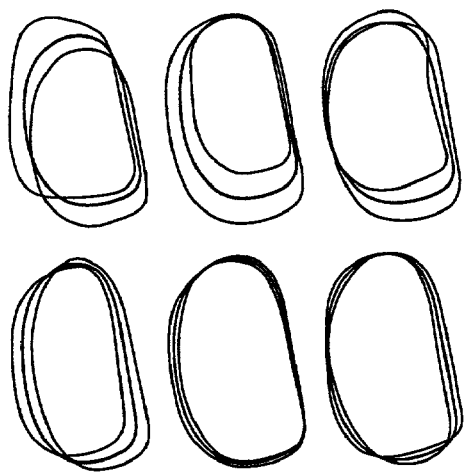
FIG. 5 illustrates components of a PCA decomposition.
Figure 6:
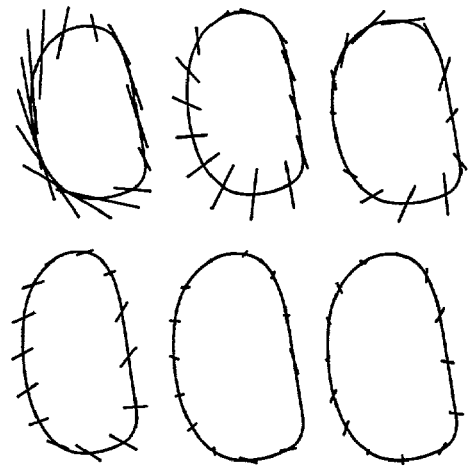
FIG. 6 illustrates the components of FIG. 5 in a different way.
Figure 7A:
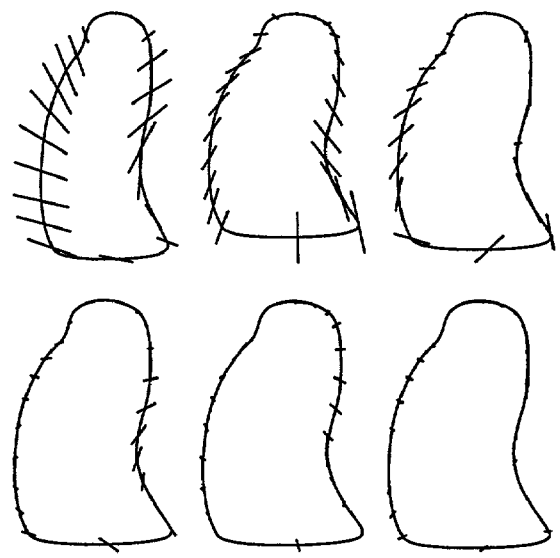
FIG. 7(a) illustrates PCA-based components for an image sequence.
Figure 7B:
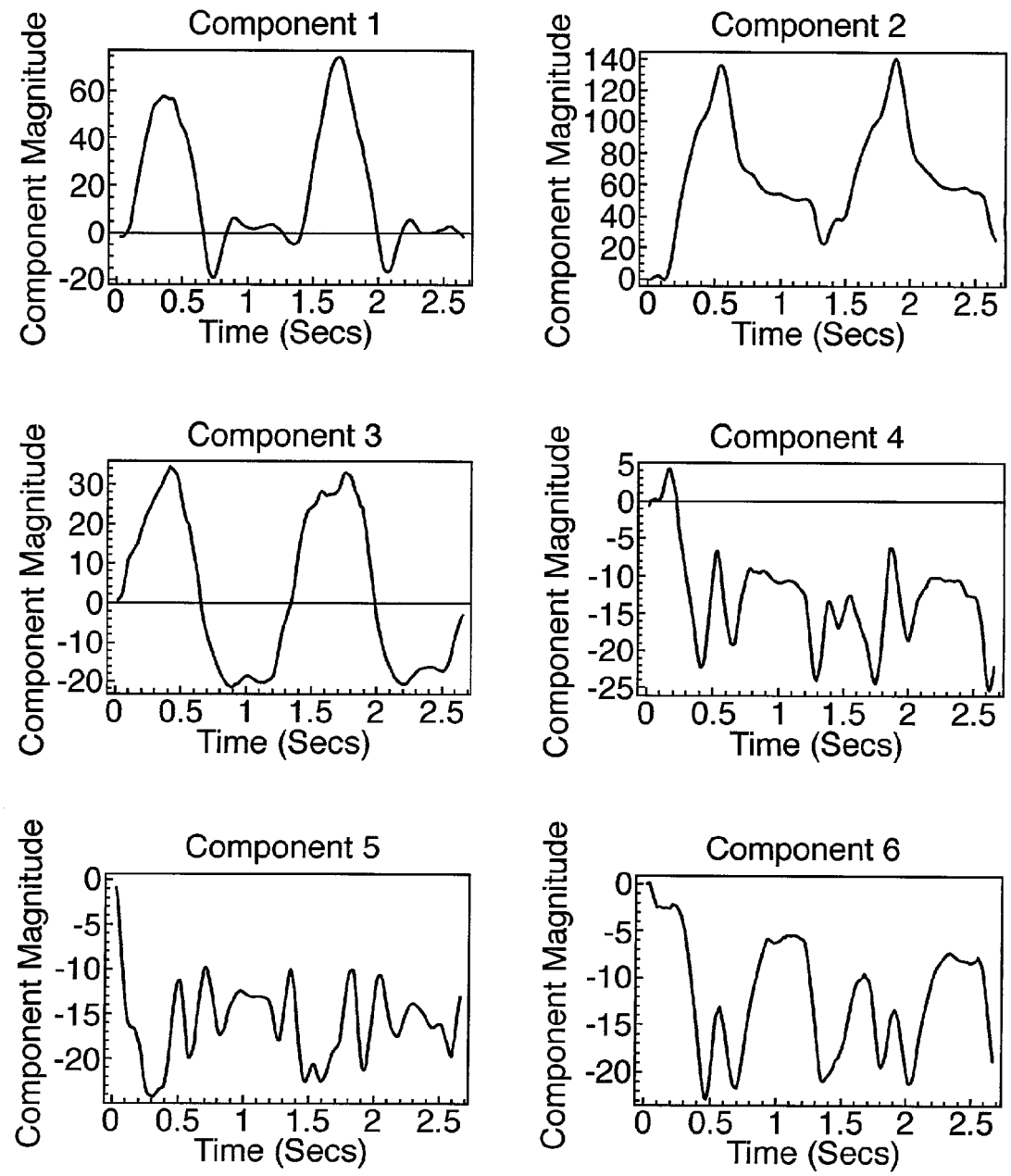
FIG. 7(b) shows the variation with time of the components of FIG. 7(a)
Figure 8:
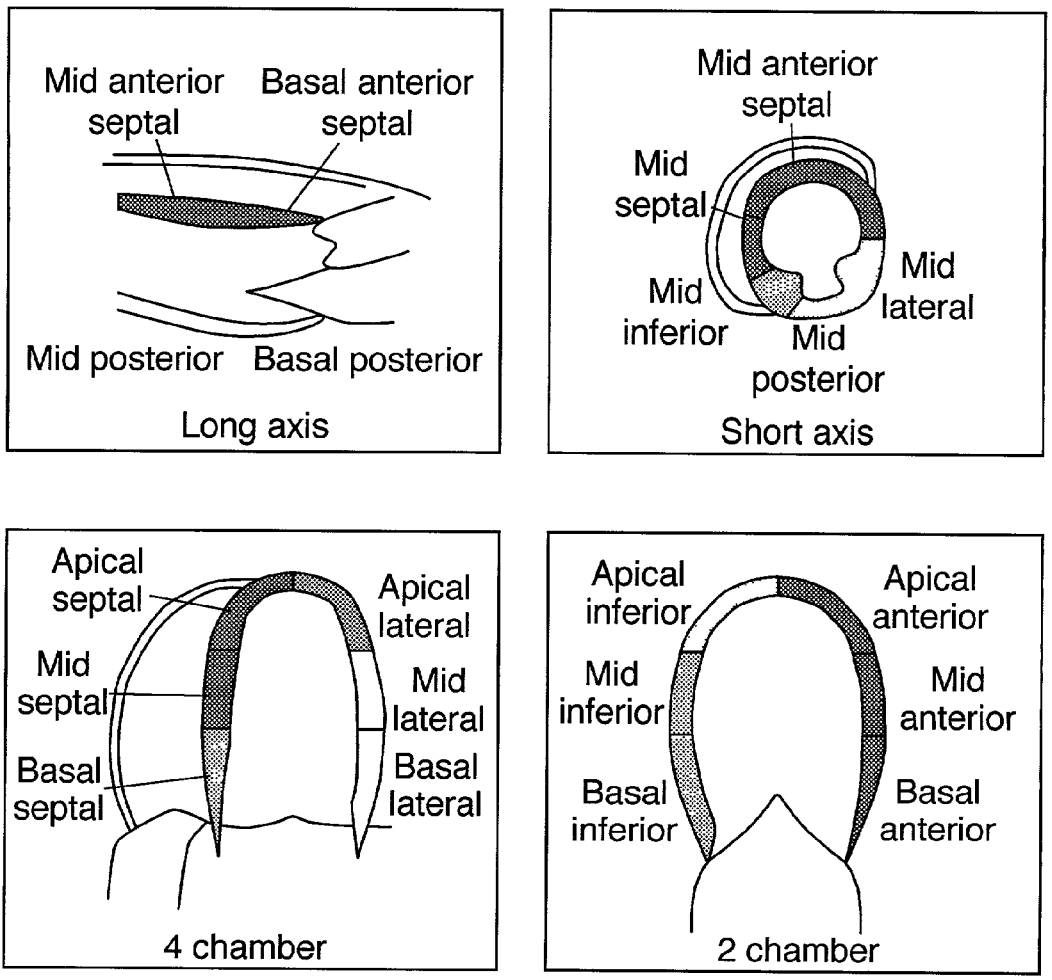
FIG. 8 illustrates the sixteen-segment anatomical model of the heart.

First of all an embodiment of the invention will be described which is for providing clinically significant quantitative data from an echocardiographic image sequence in which the endocardial wall of the left ventricle has been tracked, for instance using the technique described in Jacob et al mentioned above. It will be recalled that the tracking of the endocardial wall can be defined in terms of the movement of the control points of the spline curve as:—

$$Q=Q_0+W_{PCA}X_{PCA}$$

Where the subscript "PCA" indicates that the tracking is based on a principal component analysis. The time varying part is the shape-vector X which can be recovered using a pseudo inverse of the shape-space $W_{PCA}$:—

$$X_{PCA}=W^*_{PCA}(Q-Q_0)$$

where $W^*_{PCA}$ represents the pseudo inverse. However, it will be recalled that FIG. 7 demonstrates that it is not easy to place any clinical significance on the time varying components of X.

With this embodiment of the present invention, however a new shape space can be used for decomposing the results of tracking. This can be termed an "interpretational shape-space" and it can be selected to derive from the positions of the control points through the sequence time varying values of clinical interest. In matrix notation this can be explained as:—

$$X_{CLIN}=W^*_{CLIN}(Q-Q_0)$$

Figure 9:
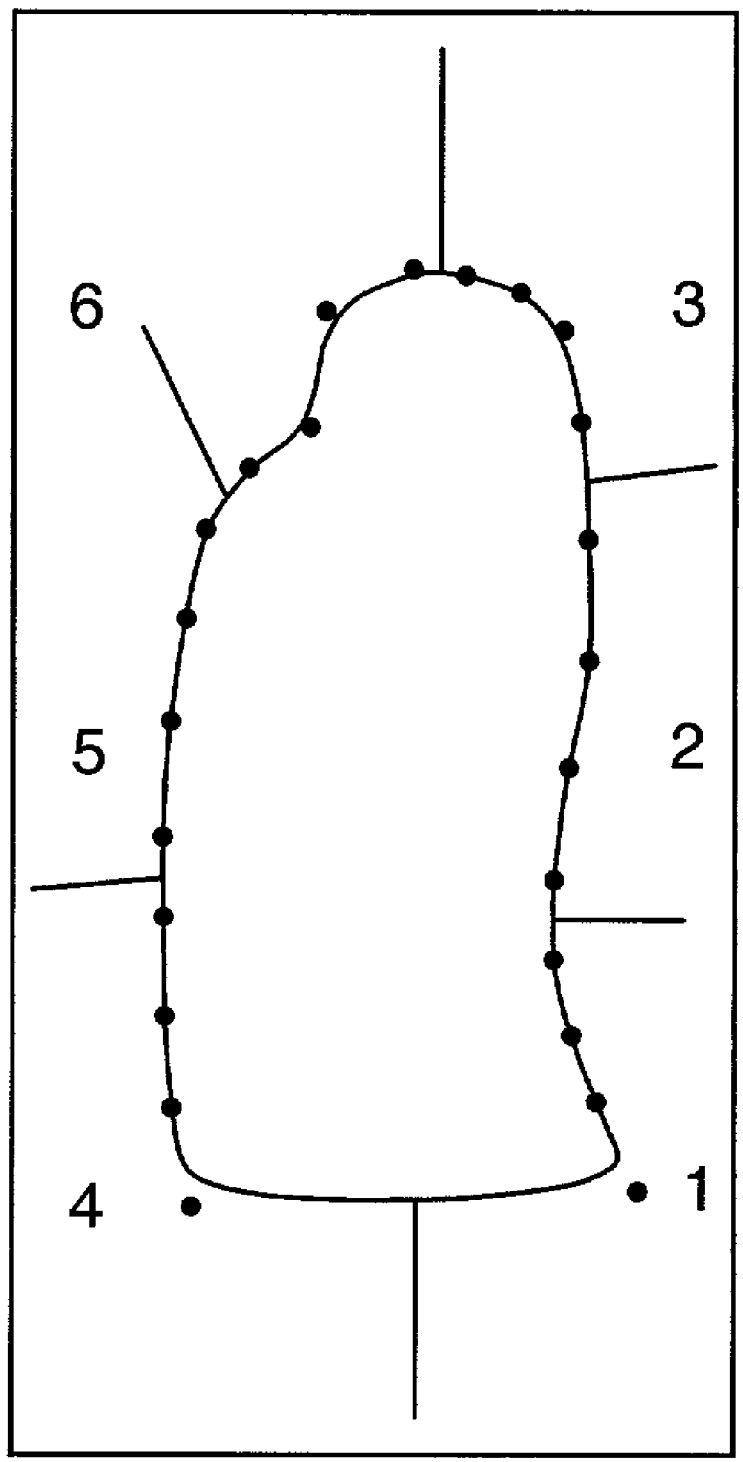
FIG. 9 illustrates schematically the positioning of control points for a B-spline and the position of the segments of the boundary.

Recalling that the components of Q are the coordinates (in 2D just the x and y coordinates) of the control points, the interpretational shape-space can be selected so that the components of $X_{CLIN}$ represented the movement of only certain control points. For instance, if there are four control points for each segment as illustrated in FIG. 9, then the interpretational shape-space can be defined so that the components of X resulting from the matrix multiplication will be an average of the amount of movement of the control points in each segment. To achieve this each row of $W^*_{CLIN}$ has four non-zero weights to pick-out the four x and y coordinates of the four control points in a segment, the rest of the row being zeros. Thus the position 1 to 4 of the first row of $W^*_{CLIN}$ can be ¼, with the rest zero to form, after multiplication, an average of the x-coordinates of the control points in the first segment. In the second row positions 5 to 8 are ¼, with the rest zero and so on. Thus, without writing the whole matrix out, $W^*_{CLIN}$ can be as follows:—

$$W^*_{CLIN} = \begin{pmatrix} \frac{1}{4} & \frac{1}{4} & \frac{1}{4} & \frac{1}{4} & 0 & 0 & 0 & 0 & \cdots & 0 & 0 & 0 & 0 \\ 0 & 0 & 0 & 0 & \frac{1}{4} & \frac{1}{4} & \frac{1}{4} & \frac{1}{4} & \cdots & 0 & 0 & 0 & 0 \\ 0 & 0 & 0 & 0 & 0 & 0 & 0 & 0 & \ddots & 0 & 0 & 0 & 0 \\ 0 & 0 & 0 & 0 & 0 & 0 & 0 & 0 & & 0 & 0 & 0 & 0 \\ 0 & 0 & 0 & 0 & 0 & 0 & 0 & 0 & \cdots & 0 & 0 & 0 & 0 \\ 0 & 0 & 0 & 0 & 0 & 0 & 0 & 0 & \cdots & \frac{1}{4} & \frac{1}{4} & \frac{1}{4} & \frac{1}{4} \end{pmatrix}$$

Thus, in 2D, if the positions of the first four control points (i.e. for the (basal inferior segment) are written at time $t_0$ as:—

$(x_1^0, y_1^0), (x_2^0, y_2^0), (x_3^0, y_3^0), (x_4^0, y_4^0)$ and at time t, as:—

$(x_1^t, y_1^t), (x_2^t, y_2^t), (x_3^t, y_3^t), (x_4^t, y_4^t)$, then $Q_0 = (x_1^0 x_2^0 x_3^0 x_4^0 \ldots x^{n-3 0} x_{n-2}^0 x_{n-1}^0 x_n^0 x_n^0 y_1^0 y_2^0 y_3^0 y_4^0 \ldots y_{n-3}^0 y_{n-2}^0 y_{n-1}^0 y_n^0)^T$
and $Q_1 = (x_1^t x_2^t x_3^t x_4^t \ldots x_{n-3}^t x_{n-2}^t x_{n-1}^t x_n^t y_1^t y_2^t y_3^t y_4^t \ldots y_{n-3}^t y_{n-2}^t y_{n-1}^t y_n^t)^T$ and it can be seen that the effect of multiplying $Q-Q_0$ by the interpretational shape-space matrix $W^*_{CLIN}$ means that the components of $X_{CLIN}$ are just the averages of the x and y components of each of the segments. Thus the first component of $X_{CLIN}$ is just:—

¼ $\{(x_1^0-x_1^t)+(x_2^0-x_2^t)+(x_3^0-x_3^t)+(x_4^0-x_4^t)\}$

The same is true for the y components, and for each of the other segments.

The above interpretational shape-space is based on the use of four control points in each segment weighted equally. However, a different number of control points for each segment can be used. Further, because the control points at the end of each segment actually affect the spline curve in the next segment, it is also possible to adjust the value of the components in the interpretational shape-space to favour the control points in the middle of each segment. For instance instead of the components (¼, ¼, ¼, ¼), one could set the components as (⅙, ⅓, ⅓, ⅙) for each segment.

It is possible to further enhance the analysis by removing the heart's translational and rotational motion. This is because the excursion of the contour (representing the heart wall) is measured from a fixed external frame of reference. The effect of translation and rotation can be removed by subtracting out the centroid of the spline curve, so that:—

$$X_{CLIN} = W^*_{CLIN}((Q-\overline{Q})-(Q_0-\overline{Q}))$$

where $\overline{Q}$ and $\overline{Q}_0$ are the average of Q and $Q_0$ respectively.

Thus the use of this interpretational shape-space means that the shape-space vector components are meaningful in clinical terms—they represent the average function of each segment of the left ventricular boundary.

Figure 10A:
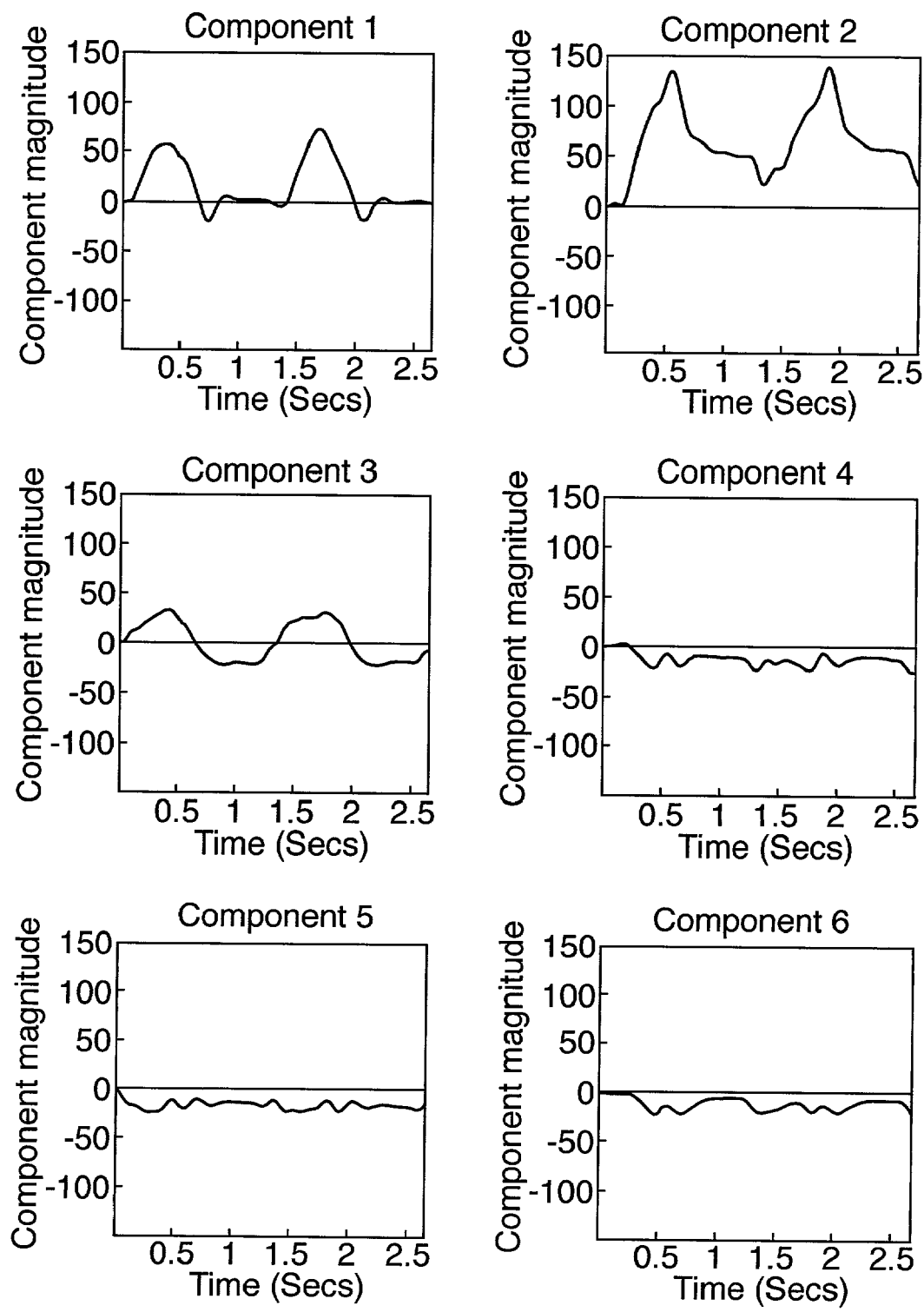
FIG. 10(a) illustrates the time variation of PCA components in an image sequence.

To show the value of this FIG. 10 compares plots of the time variation of the six components of a PCA shape-space, with the variation with time of the six components from the interpretational shape-space (i.e. the average position of the four control points for each segment). FIG. 10(a) illustrates the variation based on the PCA tracking shape-space and FIG. 10(b) the interpretational shape-space. The plots of FIG. 10(b) can be clearly related to the underlying local motion of the left ventricular boundary. Thus although FIG. 10(a) demonstrates periodicity in principally the first three of the components, it is very difficult to relate these to the underlying motion of the left ventricular boundary because each component represents motion of the whole boundary. In comparison FIG. 10(b) shows that all six of the components of the new shape-space are periodic. It can be seen that the basal interior, mid-interior, mid-inferior and basal inferior segments all move normally. The observed smaller movement in the basal inferior region is in accordance with normal heart function. However the apical inferior and apical anterior segments, although moving periodically, have a reduced endocardial wall excursion. This is in accordance with the diagnosis that this subject has a myocardial infarct in the apical region. Consequently it will be understood that illustrating the component plots from the interpretational shape-space to the clinician, gives the clinician a valuable and immediately recognisable tool for assessing heart function.

It will be appreciated that an abnormal region of heart wall may not completely fill any single segment, but could be just one part of segment, and possibly be a part of another. A measure of this can easily be derived by using the technique of this embodiment of the present invention by determining the variation in the amount of movement within each segment. In this embodiment this can be done by calculating the standard deviation in the movement of the four control points in each segment. The standard deviation is, of course, a measure of the variation in degree of movement between the different control points. If all control points moved by the same amount then the standard deviation will be low. If some move considerably more than others, the standard deviation will be high.

Figure 11A:
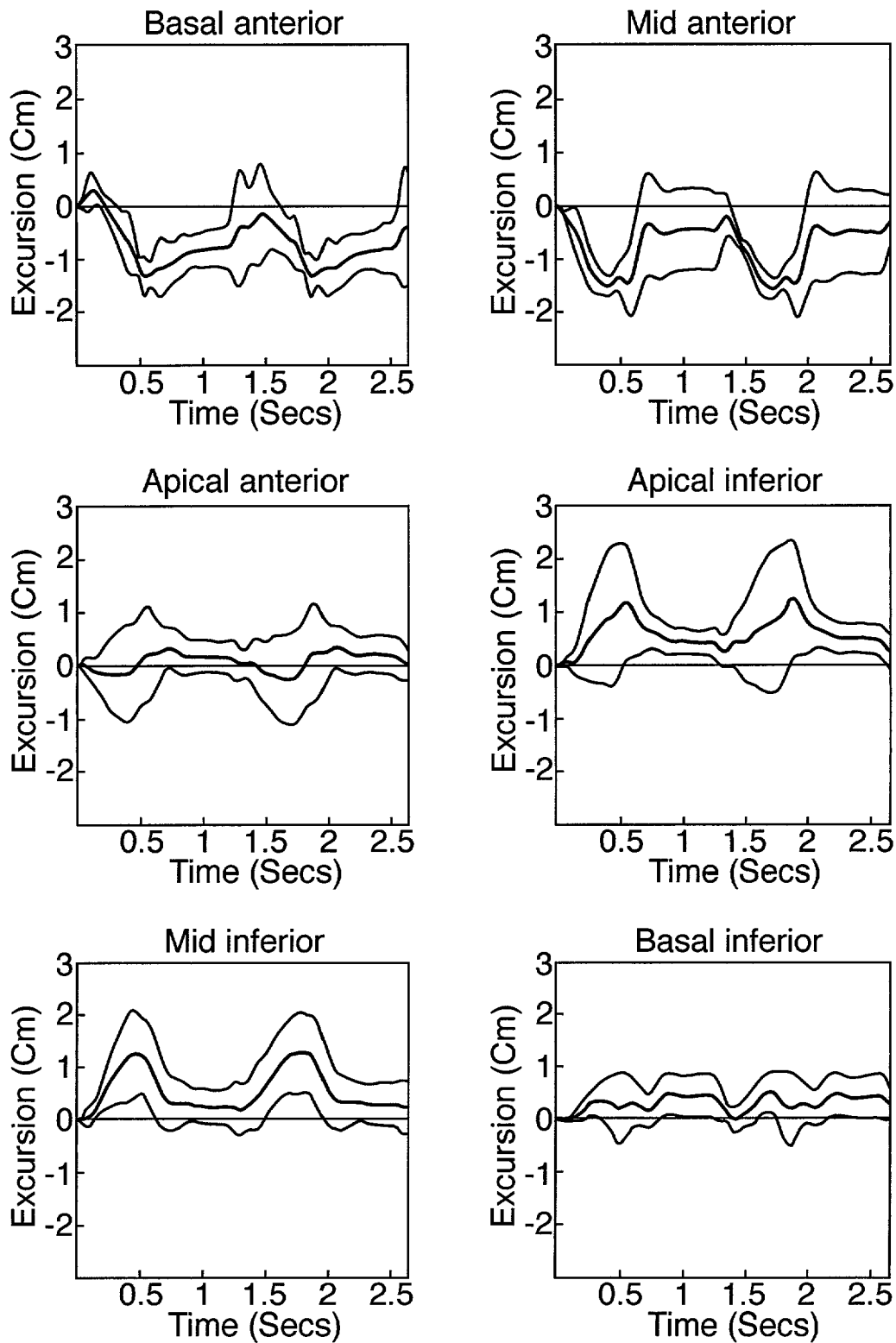
FIG. 11(a) shows plots corresponding to those in FIG. 10, but including the 95% confidence interval for the components.
Figure 11B:
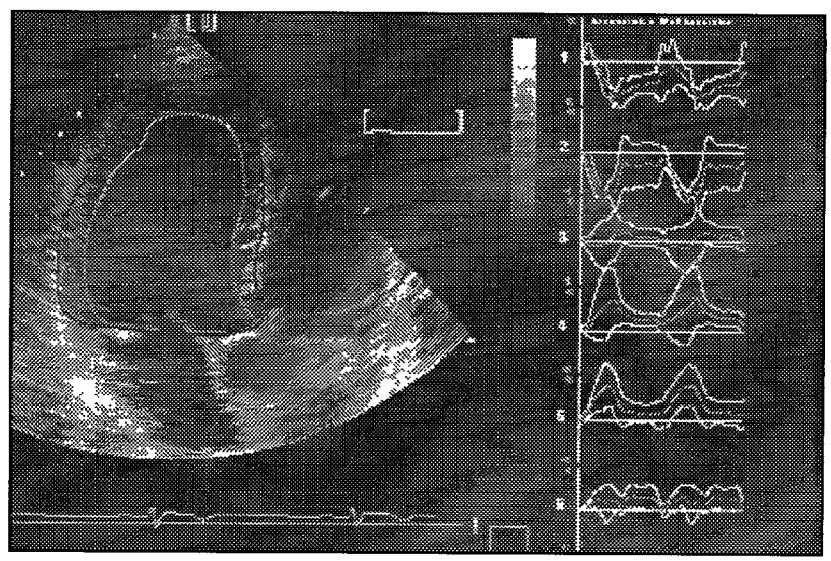
FIG. 11(b) shows how the plots of FIG. 11(a) are displayed to the clinician.

Thus, according to this embodiment, for each segment two measures are obtained, the mean and standard deviation of the endocardial wall excursion. FIG. 11(a) illustrates plots corresponding to those in FIG. 10 but including the 95% confidence interval for the interpretational shape-space vector components. From FIG. 11(a) it can be seen that the standard deviation is approximately the same in the basal interior, mid-inferior and basal inferior segments. However, the apical anterior and apical inferior segments show very noticeable increase in variation, particularly during the systolic stage of the heart cycle. This implies that not all of the apical inferior and apical anterior segments are abnormal. FIG. 11(b) shows how these plots are displayed to the clinician.

Figure 12:
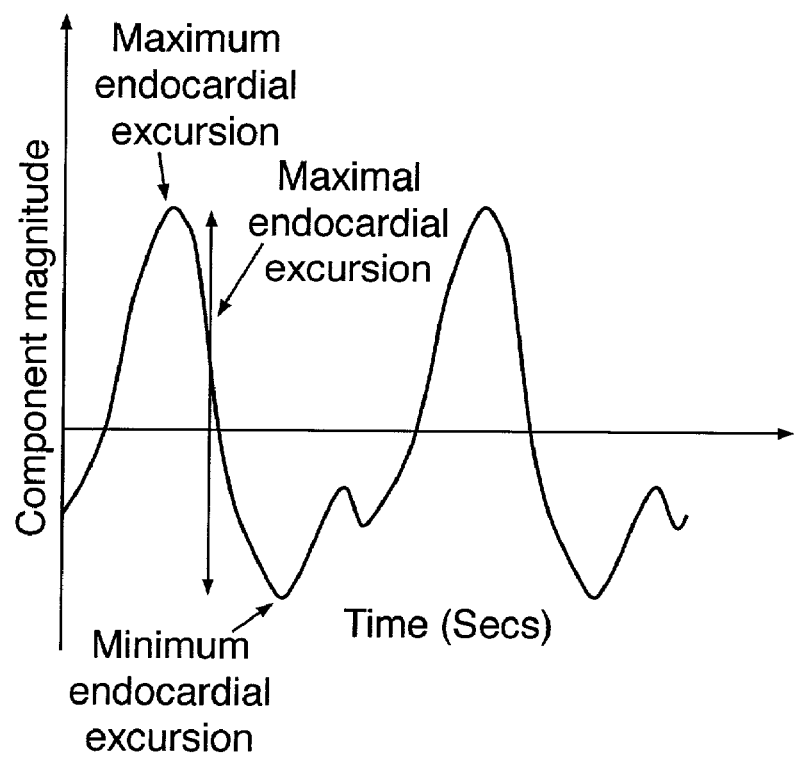
FIG. 12 illustrates calculation of the excursion of the contours tracking the endocardial boundary.
Figure 13A:
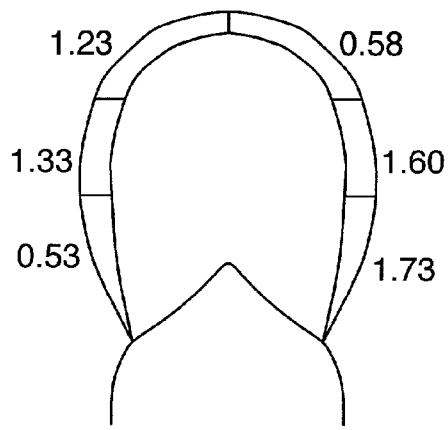
FIG. 13(a) shows the maximum wall excursion for each segment in pixels and FIG. 13(b) shows these values normalised.
Figure 13B:
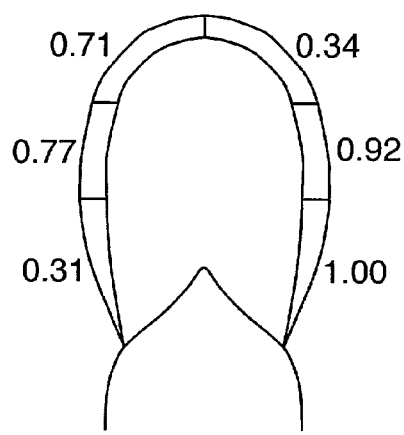

It was mentioned in the introduction that currently clinicians qualitatively score the movement of each segment. It would be useful to provide a similar scoring scheme for each segment, but which is automated and thus less subjective. In this embodiment a scoring system is provided by calculating the maximum displacement of the boundary segment. This is then normalised with respect to the maximum movement over all the six segments. The resulting number is representative of the relative maximum displacement of each segment of the endocardial wall. The wall excursion is calculated as the maximum (signed) excursion of the contour minus the minimum (signed) excursion of the contour. This is illustrated in FIG. 12. The peak-to-peak component plot is measured. FIG. 13 illustrates these values for the data from FIG. 10. FIG. 13(*a*) shows the maximum wall excursion in pixels, and FIG. 13(*b*) shows the values normalised by dividing by the largest of the six values. The relative magnitude of these values is consistent with the diagnosis of a myocardial infarct in the apical interior and apical anterior regions.

It should be noted that there is one extreme case when this scoring system will not work well. This is when every segment is abnormal, in which case each maximal endocardial wall excursion score will be small and the normalised score would appear totally normal. This can be monitored by setting a minimal allowable amplitude of the endocardial wall excursion.

It is possible to enhance the display of the results of tracking the endocardial wall by so-called "colour kinesis". In this case a number of contours are plotted together on the same image, for instance the previous 20 contours can be plotted on one image. Each contour is colour coded from the most recent in one colour, say green, to the oldest in another colour, say red. Then the wall motion is more easily recognised.

Further, it is possible to calculate the velocity at a point on the contour between each frame and its predecessor. This velocity can then be colour coded, for instance so that low velocities are coded in blue and faster velocities in red, and these velocities displayed overlying the image.

The system can further provide a way of tracking the outer boundary of the left ventricle, the epicardial wall, and of quantifying myocardial wall thickening by measuring the distance between the tracked and endocardial and epicardial walls.

It was noted in the introduction that the epicardial wall is quite difficult to track. For this reason, using a tracking strategy corresponding to that used for the endocardial wall is not possible. This embodiment of the present invention overcomes this difficulty by basing the prediction of the epicardial wall on a model of the distance between the endocardial and epicardial walls. Effectively a constraint is placed upon the distance between the two walls, and that is used to optimise the tracking of the epicardial wall.

Given an image sequence the technique involves the clinician initially manually locating and drawing around contours representing the endocardium and epicardium in a few of the image frames. Then, just as a PCA shape-space was constructed for the motions of the endocardial wall in the technique described above, a PCA shape-space is constructed in this case for the difference between the two. This is known as the "difference shape-space". Thus the difference shape-space $W_{Diff}$ is based on the PCA of the difference $Q_{Diff}$ between the control points of the epicardial wall and endocardial wall, i.e.:—

$$Q_{Diff} = Q_{EP} - Q_{EN}$$

The shape-space vector for $W_{Diff}$ is $X_{Diff}$.

The technique for finding the epicardial wall is then to use both the difference shape-space (which indicates what movement can be expected) and a search for image features representing the epicardium. This search is conducted by staring from the endocardium (whose position is more easy to establish in the image) and then searching along normals from the curve representing the endocardium. The search is for an image feature, such as a change in image intensity, representative of the epicardial wall. Then using the difference shape-space $W_{Diff}$ a contour is fitted to the measurement results.

In summary the algorithm for epicardium estimation is as follows:—

1. Obtain a shape-space, $W_{Diff}$, of the difference between the manually segmented endocardium and epicardium contours, $Q_{En,1}, Q_{En,2}, \ldots Q_{En,M}$ and $Q_{EP,1}, Q_{EP,2} \ldots, Q_{Ep,M}$, respectively.
2. Search normally to the estimated position of the endocardium, to find image measurements that represent the epicardium.
3. Using these measurements, obtain a best fitting curve, $\hat{X}_{Diff}$ (from the fitting algorithm below), in the difference shape-space, $W_{Diff}$. Call this contour $\hat{Q}_{Diff}$.
4. The estimated epicardium position, $\hat{Q}_{Ep}$, is then given by $$\hat{Q}_{Ep} = \hat{Q}_{En} + \hat{Q}_{Diff}.$$

The fitting algorithm for step 3 (taken from Blake, A. and Isard, M. (1998) "Active Contours", Springer) is as follows:

Given an initial shape estimate $\hat{r}(s)$ (or $\hat{X}$ in shape-space) with normals $\hat{n}(s)$, and a regularisation weight matrix $\hat{S}$, minimize e.g. by solving:

$$\min_x T \text{ where}$$

$$T = (X - \overline{X})^T \overline{S}(X - \overline{X}) + \sum_{i=1}^{N} \frac{1}{\sigma_i^2}(v_i - h(s_i)^T[X - \overline{X}])^2$$

Algorithm

1. Choose samples $s_i$, i=1, ..., N, such that $$s_1 = 0, s_{i+1} = s_i + h, s_N = L.$$

2. For each i, apply some image-processing filter along a suitable line (e.g. curve normal) passing through $\overline{r}(s_i)$, to establish the position of $r_f(s_i)$.
3. Initialise $$Z_0 = 0, S_0 = 0$$

$$v_i = (r_f(s_i) - \overline{r}(s_i)) \cdot \overline{n}(s_i),$$

$$h(s_i)^T = \overline{n}(s_i)^T u(s_i) W,$$

$$S_i = S_{i-1} + \frac{1}{\sigma_i^2} h(s_i) h(s_i)^T \text{ and,}$$

$$Z_i = Z_{i-1} + \frac{1}{\sigma_i^2} h(s_i) v_i.$$

5. The aggregated observation vector is, $$Z = Z_N,$$

with associated statistical information, $$S = S_N$$

6. Finally, the best fitting curve is given in the shape-space by:

$$\hat{X} = \bar{X} + (\bar{S} + S)^{-1} Z.$$

Figure 14:
FIG. 14 shows the displayed results of tracking the endocardial wall and epicardial wall in an image sequence.

FIG. 14 illustrates the results of applying these techniques to an image sequence to detect the epicardium for frames 25, 96, 104, 109 and 114 of a sequence.

The choice of search scale for the detection of image features affects the accuracy of tracking. For example an emperically chosen constant scale of 1.14 cm (30 pixels) of gave good results on an image of 720×512 pixels. It would, however be possible to link the search scale for the epicardium to the stage of the cardiac cycle, so that the search scale would be longer in systole than in diastole.

Figure 15:
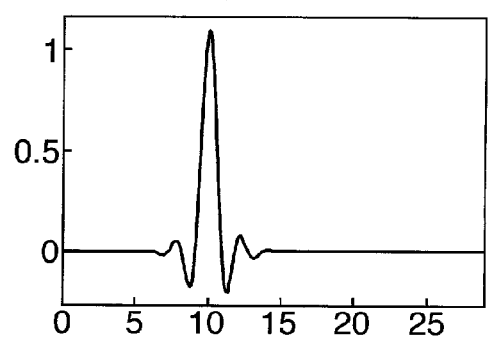
FIG. 15 illustrates a Coiffman wavelet packet.

The above technique still requires the detection of image features representing the epicardial wall, the difficulty of which has been mentioned several times. A particularly advantageous approach used in this embodiment is to plot the image intensity along the search lines (normals from the endocardial boundary) and to use a wavelet ridge detector to find the image feature corresponding to the epicardial boundary. The wavelet chosen for this embodiment was the Coiffman wavelet series. These orthogonal, compactly supported wavelets feature the highest number of vanishing moments for a given filter length. In addition, several packets within the Coiffman set have a spatial distribution that is particularly suitable for evaluating ridge-like structures (such as the epicardium) at low resolutions. Each of the profiles (such as those shown in FIG. 15) are initially dyadically-decomposed, and then reconstructed using the best-basis algorithm. Each packet within this optimised set is then compared with the total best-basis reconstruction to determine which decompositions contribute most strongly to the original profile signal. These particular low-resolution decompositions are used in the next stage of the analysis to restrict the reconstruction of the filtered profile to that of the ridge-characteristics of successive profiles. The first profile normal is chosen to be in an area of good contrast-to-noise ratio (i.e. a good profile) e.g. at the start of the basal anterior segment, with the profile normals incremented anti-clockwise from this point, with the last being at the end of the basal inferior segment.

The Coiffman wavelet with a filter length of six was chosen as it gave accurate results without imposing too heavy a computational burden.

Figure 16:
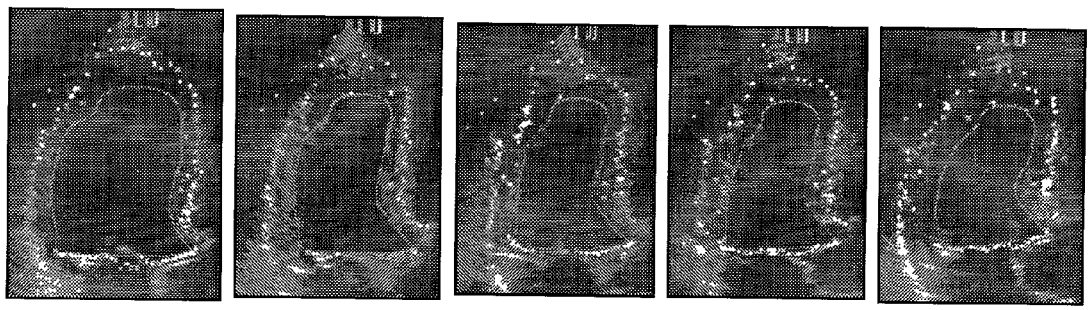
FIG. 16 illustrates the results of detecting the epicardial boundary by wavelet decomposition.

The results of detecting image features using this wavelet set are shown in FIG. 16. It is possible to further improve the detection by using information obtained along one search line in the search along the next search line.

Figure 17:
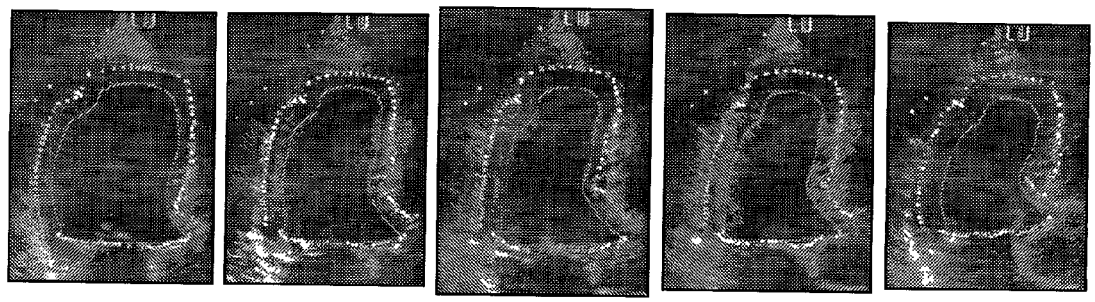
FIG. 17 illustrates the improved results using information assimilated from previous search lines.

To do this peak or ridge-like features found along a search line are negatively weighted if: (1) they deviate outside the estimated image space for the myocardium (given by the tracking above) or (2) if local maxima deviate too greatly from an allowable curvature of the epicardial boundary. Thus once the decomposed profile has been adjusted to reflect ridge localisation in the previous profiles, the low-resolution representation is then adjointly convolved with the low and high-pass quadrature filters for reconstruction. The reconstructed profile has now been smoothed (due to the use of a limited number of packets for reconstruction), shifted and normalised (due to the low-resolution weighting function); then a ridge detection that finds the maximum of the reconstructed profile is applied to this. The net result is that the ridge detection is much more consistent with the visual location of the epicardium, as FIG. 17.

It will be noted that in the basal anterior segment, localisation is poorer than on other parts of the epicardial boundary. The reason for this is that the mitral valve is positioned here and the curvature of the boundary deviates too much from the allowable curvature. However, the localisation is improved for the rest of the epicardial boundary.

An example of the results of this technique are illustrated in FIG. 18. FIG. 18(a) shows the endocardial and epicardial walls and FIG. 18(b) illustrates the myocardial thickening which occurs through the sequence. This is illustrated by colouring the region between tracked epicardial and endocardial walls.

Just as the regional wall excursion, i.e. the movement of the endocardial wall in the different segments was quantified, it is useful also to quantify myocardial thickening for the segments. This can be done by calculating the average distance between the epicardial and endocardial boundaries. An alternative is to use the difference shape-space and associated shape-space vector $W_{Diff}$ and $X_{Diff}$. The values of these can be integrated over the individual segments to provide a measure of the myocardial thickness in that segment. A plot of this value for each segment through an image sequence is shown in FIG. 19. It can be seen at the basal inferior, mid-anterior, mid-inferior and basal inferior segments all move normally. The smaller thickening the basal anterior region is also normal. However, the reduced change in thickness in the apical anterior and apical inferior segments is abnormal and agrees with the diagnosis that this patient has a myocardial infarct in the apical region.

Figure 20:
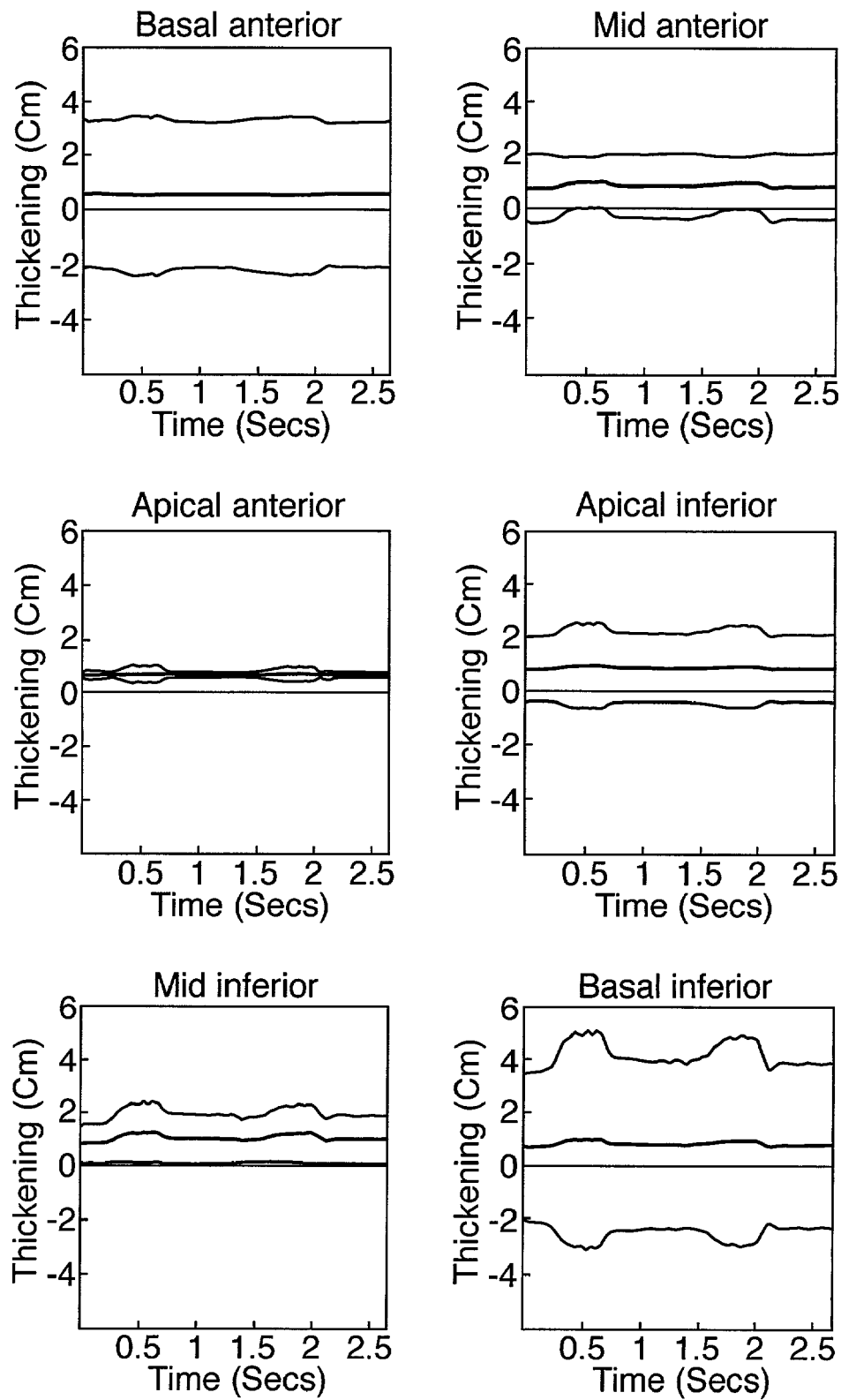
FIG. 20 illustrates the variation in thickening within each segment.

It is also useful to look at the variation in segment wall thickening in each of the six segments as shown in FIG. 20. The starting point for this data set is diastole, with the heart entering systole after around a tenth of a second. The basal anterior and basal inferior segments show a lot of variation in wall thickness. The lack of thickening and variation is the apical anterior segment is consistent, again, with the above diagnosis. However, there is more variation in the apical inferior, than in the apical anterior segment. This implies that not all of the apical inferior segment is ischemic. Thus again the measurement of variation in individual segments gives an idea of whether it is the whole segment or only part of the segment which is abnormal.

Figure 21:
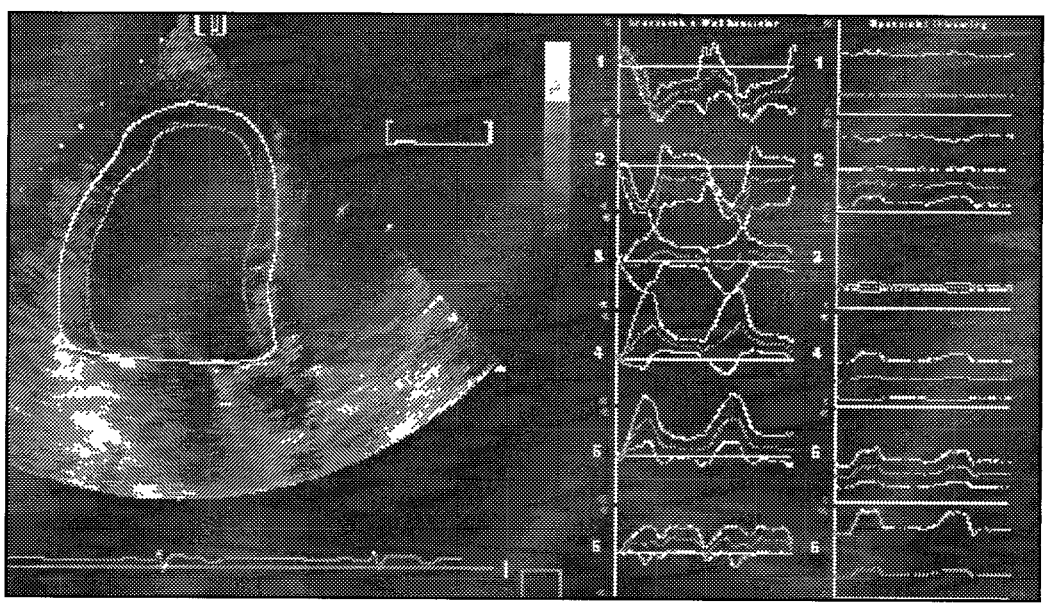
FIG. 21 illustrates the thickening information as it might be displayed to a clinician.

FIG. 21 illustrates the data as it might be presented to a clinician. Thus the endocardial and epicardial walls are overlayed on the image and track movement of the ventricle. Plots of endocardial wall excursion and myocardial thickening, including the variation within each segment are illustrated alongside. Thus the clinician can easily recognise from the plots abnormal areas of the left ventricular wall.

A single numerical score representative of wall thickening can also be calculated as follows:—

$$\% Th = \frac{Th_{ES} - Th_{ED}}{Th_{ED}} \times 100$$
$$= \left(\frac{Th_{ES}}{Th_{ED}} - 1\right) \times 100.$$

Where, $Th_{ES}$ is the thickness of the myocardial segment at end-systole, and $Th_{ED}$ is the thickness of the myocardial segment at end-diastole (in cm).

Figure 22A:
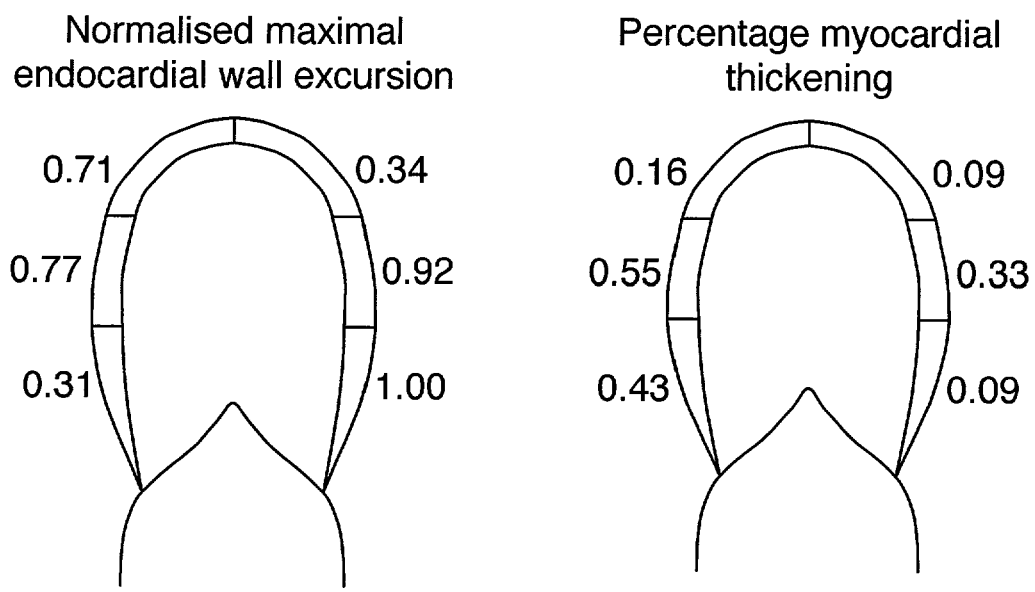
FIG. 22(a) shows the normalised maximal endocardial wall excursion for the data of FIG. 13 and the percentage myocardial thickening scores for the same data.
Figure 22B:
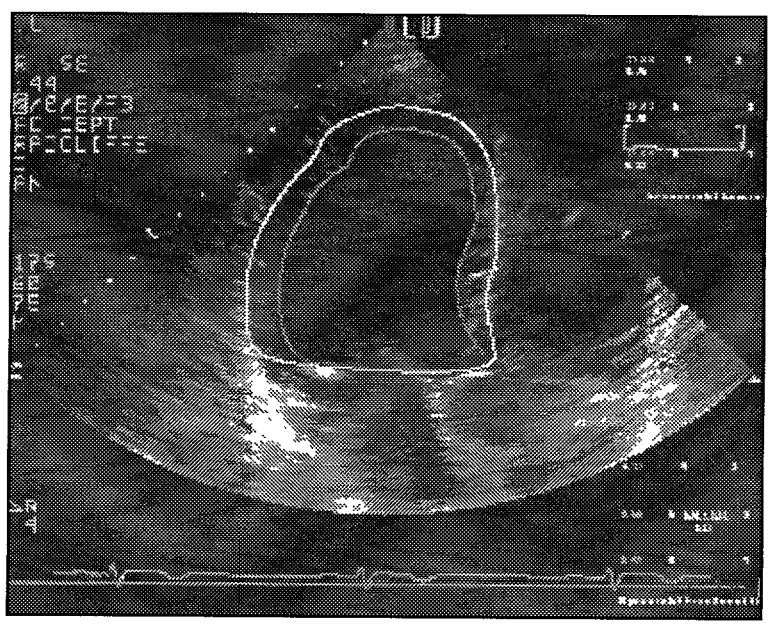
FIG. 22(b) illustrates the endocardial wall excursion and myocardial thickening scores in the form in which they are presented to the clinician.

Scores of regional percentage of wall thickening for the data in FIG. 13 are shown in FIG. 22. FIG. 22(a) shows the normalised maximal endocardial wall excursion for FIG. 13, FIG. 22(b) shows the percentage myocardial thickening and FIG. 22(c) illustrates the interface in the form presented to the clinician.

To further enhance the display the technique of colour kinesis mentioned previously can also be used. In this case the change in thickness between a frame and its predecessor is calculated, and these cumulative distances are colour coded so that the most recent is in one colour, say blue, and the oldest is in another colour, say red. Thus a plot of the previous 20 frames can be made on the same axis with time being illustrated by changing colour.

While the above embodiment has been described with reference to the analysis and interpretation of echocardiograms, it will be appreciated that the techniques are applicable to any image sequence of the non-rigid motion of a deformable object. Thus this includes ultrasound images of other organs or other objects, as well as images obtained of human organs or other objects by other imaging modalities.

What is claimed is:

1. A method of analysing a sequence of images of a deformable object in non-rigid motion, comprising:
   detecting the boundary of the object in each image of the sequence and fitting a non-rigid contour to the detected boundary;
   tracking the boundary through the sequence by calculating a shape-space representation with respect to a first shape-space of the movement of the non-rigid contour through the sequence;
   defining a second, different shape-space whose shape vector comprises components corresponding to a desired attribute of the motion; and
   calculating from the tracked boundary the shape-vector corresponding to the different shape-space.

2. A method according to claim 1, wherein the non-rigid contour is a spline curve.

3. A method according to claim 2, further comprising visually locating the boundary in only some selected images in the sequence and fitting the spline curve to the visually located boundary in each selected image by calculation of the control points for the spline curve.

4. A method according to claim 3, wherein the first shape-space representation represents the movement of the spline curve control points through the selected images.

5. A method according to claim 3, further comprising predicting the position of the boundary in each frame of the sequence based on the spline curve, detecting image features representative of the boundary in the vicinity of the predicted position of the boundary, and correcting the predicted position on the basis of the detected image features.

6. A method according to claim 2, further comprising displaying the spline curve overlying the image.

7. A method according to claim 2, further comprising calculating and outputting for each of the segments an average of the amount of movement of control points of the spline curve for that segment.

8. A method according to claim 7, wherein the average is weighted in favour of spline curve control points in the middle of each segment.

9. A method according to claim 2, further comprising calculating and outputting for each of the segments a measure of the variation in the amount of movement of control points of the spline curve for that segment.

10. A method according to claim 2, further comprising calculating and outputting for each of the segments a measure of the maximal excursion of control points of the spline curve for that segment.

11. A method according to claim 2, further comprising from calculating control points of the spline curve the shape-vector corresponding to the different shape-space.

12. A method according to claim 11, wherein a pseudo-inverse of the different shape-space space is defined to produce as components of the shape-vector a measure of the movement of the spline curve control points for each of the segments.

13. A method according to claim 12, further comprising displaying graphically the variation through the sequence of the shape-vector components.

14. A method according to claim 2, wherein four spline function control points are defined for each of the segments.

15. A method according to claim 1, wherein the shape-space is calculated by performing a principal component analysis (PCA) of the movement of the boundary through the selected images.

16. A method according to claim 1 wherein the boundary is an inner boundary of a wall of the object, and the method further comprises:
   searching outside the inner boundary for image features representing an outer boundary of the wall of the object.

17. A method according to claim 16, further comprising fitting a spline curve to the detected image features representing the outer boundary.

18. A method according to claim 17, wherein the spline curve is fitted by:
   manually locating the inner and outer boundaries in only some images of the sequence;
   calculating a shape-space for the change through the sequence of the distance between the two boundaries;
   detecting the inner boundary and performing the search outside the inner boundary for image features representing the outer boundary in images of the sequence; and
   fitting a spline curve to the detected image features in the other images of the sequence by using the shape-space.

19. A method according to claim 18, further comprising performing a principal component analysis of the change in the distance between the two boundaries, as a basis for the shape-space.

20. A method according to claim 18, wherein, when fitting the spline curve to the detected image features, the detected image features are weighted down if they imply a difference between the inner and outer boundaries which lies outside the shape-space space for that difference.

21. A method according to claim 17, wherein, when fitting the spline curve to the detected image features, the detected image features are weighted down if they imply a high curvature of the outer boundary.

22. A method according to claim 16, wherein the searching outside the inner boundary for image features representing the outer boundary comprises detecting and analysing changes in the image intensity outwards from the inner boundary.

23. A method according to claim 22, further comprising detecting a ridge in a plot of the image intensity outwards from the inner boundary.

24. A method according to claim 23, further comprising performing a wavelet decomposition of the plot of the image intensity to smooth the plot and detecting as the ridge a maximum in the smoothed plot.

25. A method according to claim 22, wherein the search is conducted along a plurality of search lines spaced along and extending radially outwardly from the said inner boundary.

26. A method according to claim 16, wherein the images are ultrasound images.

27. A method according to claim 16, wherein the object is a human or animal organ.

28. A method according to claim 16, wherein the object is a human or animal heart.

29. A method according to claim 28, wherein the object is the left or right ventricle.

30. A method according to claim 28, further comprising graphically displaying the change through the sequence of the distance between the inner and outer boundaries as a representation of myocardial thickening.

31. A method according to claim 28, further comprising segmenting the wall of the heart and graphically displaying for each segment the change through the sequence of the distance between the inner and outer boundaries as a representation of myocardial thickening for that segment.

32. A method according to claim 31, wherein the distance between the inner and outer boundaries is averaged or integrated for within each segment.

33. A method according to claim 31, further comprising calculating the variation within each segment of the change through the sequence of the distance between the inner and outer boundaries.

34. A computer program storage medium readable by a computer system and tangibly embodying a computer program comprising computer-executable instructions for performing the method of claim 1.

35. A method according to claim 1, wherein the components of the shape-vector correspond to the movement of different segments of the detected boundary.

36. A method according to claim 35, further comprising of displaying graphically the calculated amount of movement of each of the segments of the detected boundary.

37. A method according to claim 35, further comprising calculating and outputting for each of the segments of the detected boundary an average of the amount of movement of that segment.

38. A method according to claim 35, further comprising calculating for each of the segments of the detected boundary the variation in the amount of movement within that segment.

39. A method according to claim 35, further comprising calculating for each of the segments the maximal excursion of the detected boundary during the non-rigid motion.

40. A method according to claim 35, wherein the object is an internal body organ of a human or animal and the segments are clinically-significant segments of the organ.

41. A method according to claim 40, wherein the images are produced by a technique selected from the group consisting of: ultrasound-based, MR-based and x-ray based, imaging and nuclear medicine.

42. A method of analysing a sequence of images of an internal body organ in non-rigid motion, comprising:
   detecting the boundary of the organ in each image of the sequence; and
   automatically calculating the amount of movement through the sequence of each of a plurality of clinically significant segments of the detected boundary,
   wherein a spline curve is fitted to the boundary and the method further comprises calculating and outputting for each of the clinically significant segments an average of the amount of movement of the spline curve control points for that segment, the average being weighted in favour of spline curve control points in the middle of each segment.

43. A method of analysing a sequence of images of a deformable object in non-rigid motion to detect inner and outer boundaries of a wall of the object, the method comprising:
   detecting the inner boundary; and
   searching outside the inner boundary for image features representing the outer boundary,
   wherein the method further comprises fitting a spline curve to the detected image features representing the outer boundary,
   wherein the spline curve is fitted by:
      manually locating the inner and outer boundaries in only some images of the sequence;
      calculating a shape-space for the change through the sequence of the distance between the two boundaries;
      detecting the inner boundary and performing the search outside the inner boundary for image features representing the outer boundary in images of the sequence; and
      fitting a spline curve to the detected image features in the other images of the sequence by using the shape-space; and
   wherein, when fitting the spline curve to the detected image features, the detected image features are weighted down if they imply a difference between the inner and outer boundaries which lies outside the shape-space for that difference.

44. A method of analysing a sequence of images of a deformable object in non-rigid motion, the method comprising:
   modeling the boundary using a non-rigid contour;
   calculating a representation of movement of the contour through the sequence of images using a tracking shape-space; and
   decomposing the calculated movement representation using an interpretational shape-space shape space that is different than the tracking shape-space.

45. A method according to claim 44, wherein the non-rigid contour is a spline curve.

46. A method according to claim 44, further comprising: displaying the decomposed movement representation.

47. A method according to claim 44, further comprising: generating numerical values corresponding to the decomposed movement representation.

48. A computer-readable medium on which computer-executable instructions for implementing the method of claim 44 are tangibly embodied.

* * * * *